(12) United States Patent
Hartgerink et al.

(10) Patent No.: US 9,228,009 B2
(45) Date of Patent: Jan. 5, 2016

(54) MULTI-HIERARCHICAL SELF-ASSEMBLY OF A COLLAGEN MIMETIC PEPTIDE

(71) Applicant: WILLIAM MARSH RICE UNIVERSITY, Houston, TX (US)

(72) Inventors: Jeffrey D. Hartgerink, Pearland, TX (US); Lesley R. O'Leary, Houston, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 0 days.

(21) Appl. No.: 14/176,235

(22) Filed: Feb. 10, 2014

(65) Prior Publication Data

US 2014/0187651 A1    Jul. 3, 2014

Related U.S. Application Data

(63) Continuation of application No. PCT/US2012/050323, filed on Aug. 10, 2012.

(60) Provisional application No. 61/522,119, filed on Aug. 10, 2011.

(51) Int. Cl.
*C07K 14/78* (2006.01)
*A61L 27/24* (2006.01)
*A61L 27/52* (2006.01)
*A61L 27/54* (2006.01)

(52) U.S. Cl.
CPC .................. *C07K 14/78* (2013.01); *A61L 27/24* (2013.01); *A61L 27/52* (2013.01); *A61L 27/54* (2013.01)

(58) Field of Classification Search
CPC ... A61K 38/00; A61K 38/17; A61K 38/1709; A61K 47/48784; A61K 9/4825; C07K 14/78; A61L 2300/45; A61L 31/145; A61L 27/24
See application file for complete search history.

(56) References Cited

PUBLICATIONS

Merrett et al. Synthetic neoglycopolymer-recombinant human collagen hybrids as biomimetic crosslinking agents in corneal tissue engineering. Biomaterials. Oct. 2009;30(29):5403-8.*

* cited by examiner

*Primary Examiner* — Karlheinz R Skowronek
*Assistant Examiner* — Jia-Hai Lee
(74) *Attorney, Agent, or Firm* — Reed Smith LLP; Robert R. Riddle

(57) ABSTRACT

The present disclosure generally relates to collagen, and more particularly compositions and methods related to collagen-mimetic peptides. More specifically, the present disclosure provides a collagen-mimetic peptide and peptide systems comprising the amino acid sequence (Pro-Lys-Gly)$_4$(Pro-Hyp-Gly)$_4$(Asp-Hyp-Gly)$_4$.

15 Claims, 13 Drawing Sheets

MULTI-HIERARCHICAL SELF-ASSEMBLY OF A COLLAGEN MIMETIC PEPTIDE

CROSS-REFERENCE TO RELATED APPLICATIONS

This application claims priority to PCT/US12/50323, filed Aug. 10, 2012 which claims priority to U.S. Provisional Patent Application Ser. No. 61/522,119, filed Aug. 10, 2011, both of which are incorporated herein by reference.

STATEMENT REGARDING FEDERALLY SPONSORED RESEARCH OR DEVELOPMENT

This invention was made with government support under Grant Number DMR-0645474 awarded by the National Science Foundation. The government has certain rights in the invention.

BACKGROUND

Collagen, the most abundant fibrous protein in the body, plays a major role in the structural stability of many tissues within the body (skin, tendons, cardiovascular system, cartilage, basement membranes, etc.), which make it a primary target for use in restorative medicine and other tissue-engineering applications for many different tissue types. Currently, harvested collagen that is primarily taken from bovine, porcine and human sources is used in many different clinical applications including cosmetic surgery, joint repair, artificial skin grafts, vascular tissue regeneration and even as a drug-delivery carrier. These methods follow multiple avenues for sample preparation ranging from the insertion of reconstituted collagen without the addition of any cells or growth factors into the body to the mixing of collagen with other polypeptides or polymers to form a scaffold upon which cells, growth factors and other biocompatible molecules are loaded before the complex system is implanted into the human body. And commercially available products, such as, Chondro-Gide, TransCyte, Apligraf, Integra and Matrigel demonstrate the current clinical and commercial interest in collagen-based systems.

Collagen exemplifies multi-hierarchical self-assembly. In the case of type I collagen, self-assembly begins with three 1,000 amino acid peptide strands which adopt a poly-proline type II helical structure and wind around one another forming a superhelical trimer. This structure defines the well-known collagen triple helix. These triple helices then pack against one another in quasi-hexagonal and staggered fashion, forming a nanofibrous structure known as collagen fibrils.[1,2] Collagen fibrils continue to self-assemble both linearly and laterally forming collagen fibers and a hydrogel network (FIG. 1a). Together, the multiple levels of collagen's structural hierarchy play a major role in the structural integrity of the extracellular matrix and provide binding sites for other proteins and cells.

Collagen has been the target of biomimetic design for decades due to the fact that there are many difficulties associated with the use and characterization of collagen from natural sources and by expression. The use of recombinant systems requires either genetic modifications or the use of a novel biosynthetic pathway in *E. coli* in order to express hydroxyproline-containing collagens.[3-8] Many successes have been demonstrated in the recapitulation of the collagen triple helix in short peptides, both as a homotrimer[9-17] and, more recently, as a heterotrimer.[18-24] However, examples that take these collagen-like peptides and use them to mimic the higher order assembly of collagen have faced a great deal of difficulty: in all previously reported systems, none has discretely demonstrated each level of collagen self-assembly (triple helix, nanofiber and hydrogel) within the same system. There are many examples of peptides that form organized nanostructures without gelation,[10,12,25-29] and a few have achieved gelation without proving the presence of triple helices or nanofibers,[30,31] however no system has described triple helix formation, nanofiber formation and gelation.

One example of a fiber forming collagen-like peptide was demonstrated by Chaikof and Conticello who prepared a 36 amino acid peptide with the sequence $(Pro-Arg-Gly)_4(Pro-Hyp-Gly)_4(Glu-Hyp-Gly)_4$.[32] This zwitterionic peptide was found to assemble into large organized fibers. However, even these collagen mimetic fibers have some drawbacks which include 1) a mixed composition of fibers associated with a significant quantity of other amorphous material, 2) the requirement for specific concentration and buffer composition outside of which the quality of assembly degrades or fails all together and 3) phase separation and precipitation of the formed fibers as opposed to the formation of a hydrogel.[32]

DRAWINGS

Some specific example embodiments of the disclosure may be understood by referring, in part, to the following description and the accompanying drawings.

FIG. 1 shows self-assembly of collagen type I compared to collagen mimetic peptides. (a) Scheme of type I collagen assembly in which the peptide chains (shown in red, blue and green) are 1,000 amino acids, the triple helices are 100 nm in length and blunt-ended nanofibers (shown in gray) assemble via the staggered lateral packing of the triple helices. The hydrogel image was taken of a rat-tail collagen sample. (b) Scheme for self-assembly of collagen mimetic peptides in which the peptides are 36 amino acids (shown in red, blue and green), the triple helix is staggered with a length of 10 nm and the nanofibers (shown in gray) result from triple helical elongation as well as lateral packing. The hydrogel shown is the designed peptide $(Pro-Lys-Gly)_4(Pro-Hyp-Gly)_4(Asp-Hyp-Gly)_4$.

FIG. 2 shows cartoon models of electrostatic interactions between charged amino acids in collagen mimetic peptides. Models of (a) Arg-Glu and (b) Lys-Asp charged pairs in collagen triple helices are shown.[18,24] The peptide chains are shown in red, blue and pink for (a) and red, blue and green for (b), with the highlighted hydrogen atoms in white and the highlighted oxygen atoms in pink. Distances of indicated hydrogen bonds are measured from N to O. Arg-Glu pairs do not appear to form high quality interactions due to the strong hydrogen bonding between Arg and a cross strand carbonyl oxygen which locks it into place. In contrast, two conformers of Lysine are found and both allow excellent hydrogen bonding to aspartic acid despite one of them displaying a similar hydrogen bond to a cross-strand carbonyl. (c) Chemical structures of common amino acid triplets. From top to bottom: $(Pro-Arg-Gly)_n$, $(Glu-Hyp-Gly)_n$, $(Pro-Hyp-Gly)_n$, $(Pro-Lys-Gly)_n$ and $(Asp-Hyp-Gly)_n$.

FIG. 3 shows spectroscopy graphs highlighting the triple helical nature of the designed collagen mimetic peptide. Circular dichroism spectrum shown as molar residual ellipticity (MRE) vs. wavelength (a) of fiber forming collagen like peptide $(Pro-Lys-Gly)_4(Pro-Hyp-Gly)_4(Asp-Hyp-Gly)_4$ at 0.5% and 1.0% by weight concentrations in phosphate at a temperature of 5° C. The maximum at 225 nm and minimum near 200 nm are characteristic of poly-proline type II helices. Thermal unfolding analysis curve for the peptide at 1.0% by weight concentration in phosphate, shown as (b) MRE vs. temperature and (c) first derivative of MRE vs. temperature. The cooperative transition at 41° C. demonstrates that the designed peptide forms a triple helix.

FIG. 4 shows microscopy images of (Pro-Lys-Gly)$_4$(Pro-Hyp-Gly)$_4$(Asp-Hyp-Gly)$_4$ highlighting the fibrillar assembly of the system in phosphate buffer. (a-c) TEM images of collagen-like nanofibers in phosphate taken at 40,000× magnification. (a and b) Negatively stained images of the peptide in phosphate at a concentration of 1.0% by weight that were stained with PTA, pH 6. (c) Vitreous ice cryo-TEM image of collagen-like nanofibers taken in phosphate at a concentration of 0.25% which was diluted from a 0.5% by weight sample. (d and e) AFM of collagen-like nanofibers in phosphate as observed after spin coating onto freshly cleaved mica from solutions of peptide at concentrations of 1.0% and 0.5% by weight respectively. (f and g) SEM images of critical point dried hydrogel with a peptide concentration of 1.0% by weight showing the interconnected fibrous structure responsible for the gel forming properties at 3,100× and 30,000× magnifications respectively.

FIG. 5 shows rheology of the collagen-like peptide demonstrating the temperature dependent strength of the hydrogel. (a) Strain sweep at 0.5% and 1.0% by weight peptide concentration in phosphate buffer at a temperature of 30° C. and a frequency of 1 rad/s shown as storage modulus (G') and loss modulus (G"). (b) Frequency sweep at 0.5% and 1.0% by weight peptide concentration in phosphate at a temperature of 30° C. and 1% strain shown as storage modulus (G') and loss modulus (G"). (c) Temperature dependence of rheological properties at 0.5 and 1.0% by weight peptide concentrations shown as storage modulus (G'). Data points were acquired at 1 rad/s and 1% strain. (d) Photo of the shape persistent nature of the gel with a concentration of 1.0% by weight in phosphate. The gel was prepared at a volume of 0.5 ml. Note the sustainability of the sharp gel edges.

FIG. 6 shows proposed mechanism of fiber self-assembly. (a) Peptide sequence shown as single letter amino acid code with P for proline, K for lysine, G for glycine, O for hydroxyproline and D for aspartate. Minimum repeating unit of the triple helical fiber has extensive "sticky" ends. As additional peptides (shaded grey) add to the minimum repeating unit, the percentage of amino acids forming a high quality triple helical structure rapidly increases. Positively charged lysine residues are in blue, negatively charged aspartates are in red and satisfied intrahelical electrostatic interactions are indicated by purple lassos. Available interhelical charged pair hydrogen bonds are indicated by small arrows. (b) Lysine-Aspartate interaction between the i and i+3 amino acids of adjacent peptide strands. (c) Quasi-hexagonal packing of growing fibers results in a bundle approximately 2 by 4 nm based on a triple helical cross section of 1.2 nm. (d) Fiber diffraction pattern and (e) its radially averaged intensity. Characteristic bands at 2.8 Å, 4.3 Å and 11.5 Å match well with previously reported fiber diffraction from natural collagen.

FIG. 7 shows purification of the peptide (Pro-Lys-Gly)$_4$(Pro-Hyp-Gly)$_4$(Asp-Hyp-Gly)$_4$. (a) HPLC and (b) ESI-MS data for (Pro-Lys-Gly)$_4$(Pro-Hyp-Gly)$_4$(Asp-Hyp-Gly)$_4$. Expected: 1679.8 [M+2H]$^{2+}$, Observed: 1679.7 [M+2H]$^{2+}$. Expected: 1120.2 [M+3H]$^{3+}$, Observed: 1119.8 [M+3H]$^{3+}$. Expected: 3358.6 [M+H]$^+$, Calculated: 3358.6 [M+H]$^+$ FIG. 8 shows circular dichorism thermal unfolding curves for (Pro-Lys-Gly)$_4$(Pro-Hyp-Gly)$_4$(Asp-Hyp-Gly)$_4$ in 10 mM phosphate buffer, pH 7, at varying concentrations. The melting profiles for each system are given as (a) molar residual ellipticity (MRE) vs. temperature and (b) the first derivative of MRE vs. temperature with data for 0.2% by weight concentration in black, 0.5% by weight concentration in blue and 1.0% by weight concentration in red.

FIG. 9 shows circular dichroism thermal unfolding curves for (Pro-Lys-Gly)$_4$(Pro-Hyp-Gly)$_4$(Asp-Hyp-Gly)$_4$ in 10 mM phosphate buffer at pH 3 (red) and pH 11 (blue) with a peptide concentration of 1.0% by weight. The melting profiles for each system are given as (a) molar residual ellipticity (MRE) vs. temperature and (b) the first derivative of MRE vs. temperature.

FIG. 10 shows TEM images of collagen-like nanofibers in phosphate buffer, pH 7, shown to complement FIG. 3. Negatively stained images of peptide in phosphate buffer, pH 7, at a concentration of 1.0% by weight that were stained using 2.0% by weight PTA, pH 6. Magnifications shown are 40,000× (a and b) and 60,000× (c). (d-f) Vitreous ice cryo-TEM images of collagen-like nanofibers taken in phosphate buffer, pH 7, at a concentration of 0.25% by weight diluted from a previously assembled sample at a concentration of 0.5% by weight. Image magnifications are 20,000× (d), 30,000× (e) and 40,000× (f).

Figure 13:
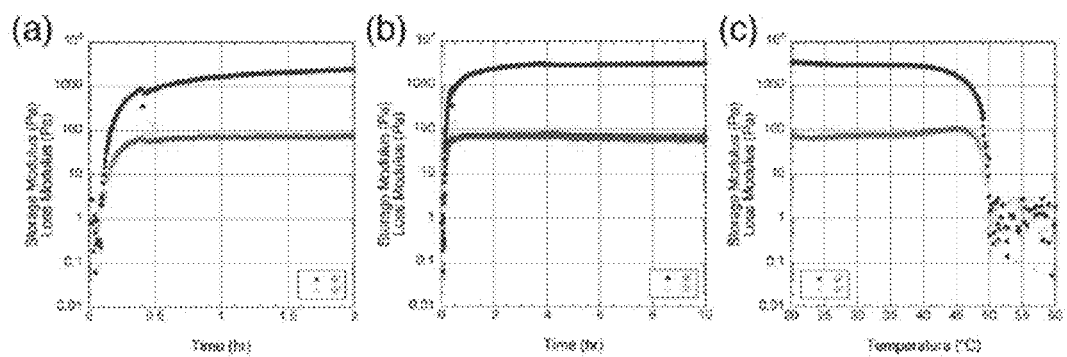

FIG. 13 shows rheological studies used to assess (a-b) the time necessary for the system to completely assemble and (c) the temperature dependence of hydrogel breakdown on (Pro-Lys-Gly)$_4$(Pro-Hyp-Gly)$_4$(Asp-Hyp-Gly)$_4$ samples in 10 mM phosphate buffer, pH 7, with a peptide concentration of 1.0% by weight. (a) Initial and (b) complete gel assembly seen via a time course rheological study run at 25° C., 1 rad/s and 0.1% strain. The sample was annealed, immediately placed on the rheometer stage with a humidity chamber present and the experiment was begun. Assembly was deemed complete when the G' leveled off A small discontinuity can be observed at approximately 0.4 hours. This is due to addition of mineral oil to prevent the hydrogel from dehydrating during the prolonged measurement. (c) Temperature ramp rheological study run from 20 to 85° C. with a ramp of 0.5° C./min and with parameters of 0.1% strain and a frequency of 1 rad/s.

Figure 14:
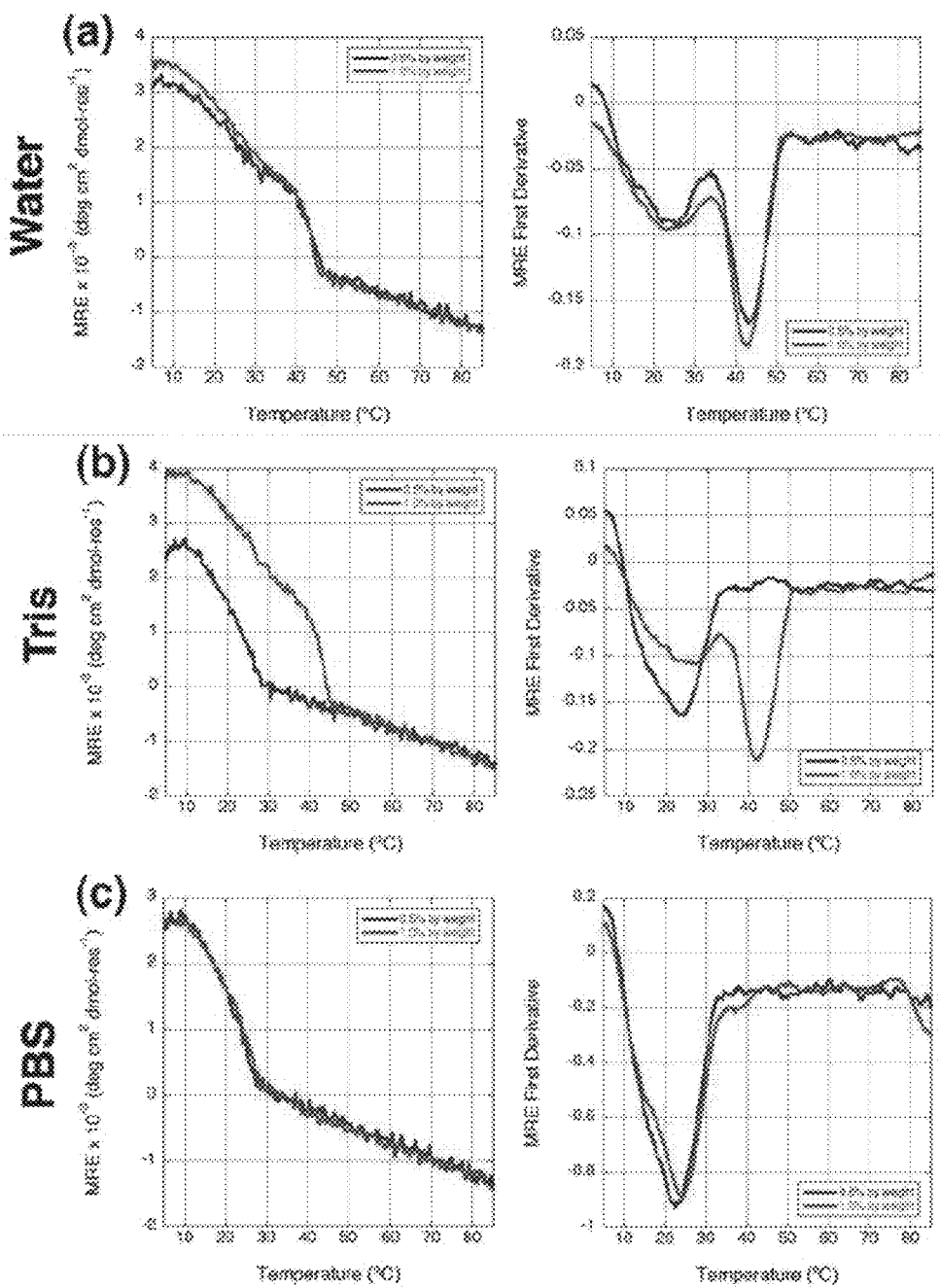

FIG. 14 shows circular dichorism thermal unfolding curves for (Pro-Lys-Gly)$_4$(Pro-Hyp-Gly)$_4$(Asp-Hyp-Gly)$_4$ in (a) water (adjusted to pH 7), (b) Tris and (c) PBS. The melting profiles for each system are given as MRE vs. temperature in the left column and the first derivative of MRE vs. temperature in the right column with data for 0.5% by weight concentration in blue and 1.0% by weight concentration in red.

Figure 15:
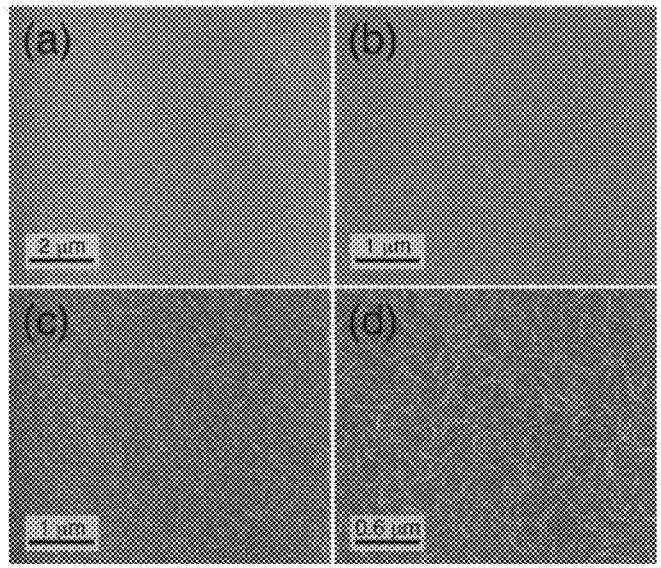

FIG. 15 shows AFM of collagen-like nanofibers in water, pH 7, as observed after spin coating the gelled samples onto freshly cleaved mica at concentrations of (a and b) 0.5% by weight and (c and d) 1.0% by weight concentrations. Nanofibers formed in water had heights of 1.2±0.3 nm.

Figure 16:
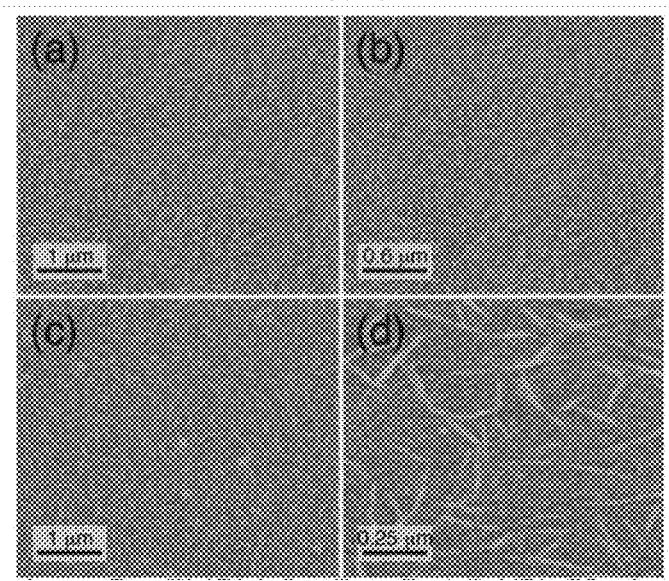

FIG. 16 shows AFM of collagen-like nanofibers in 10 mM Tris, pH 7, as observed after spin coating onto freshly cleaved mica at concentrations of (a and b) 0.5% by weight and (c and d) 1.0% by weight concentrations. Nanofibers formed in Tris had heights of 1.1±0.2 nm.

Figure 17:
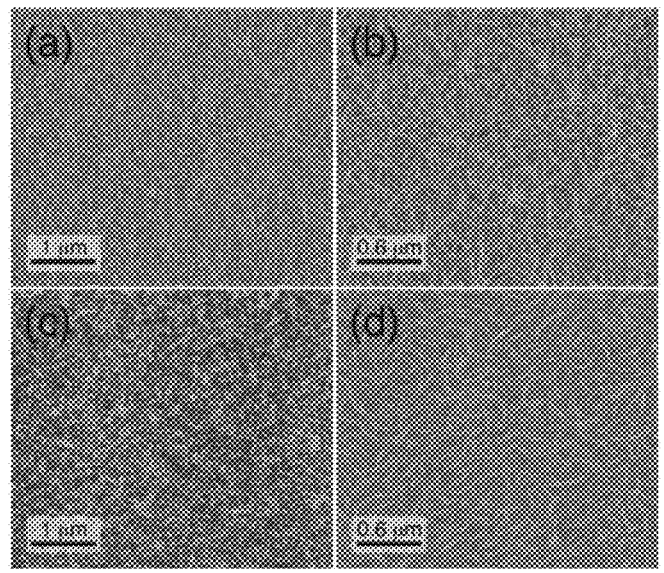

FIG. 17 shows AFM of collagen-like nanofibers in PBS, pH 7, as observed after spin coating the samples onto freshly cleaved mica at concentrations of (a and b) 0.5% by weight and (c and d) 1.0% by weight concentrations. Nanofibers formed in PBS had heights of 1.2±0.2 nm.

Figure 18:
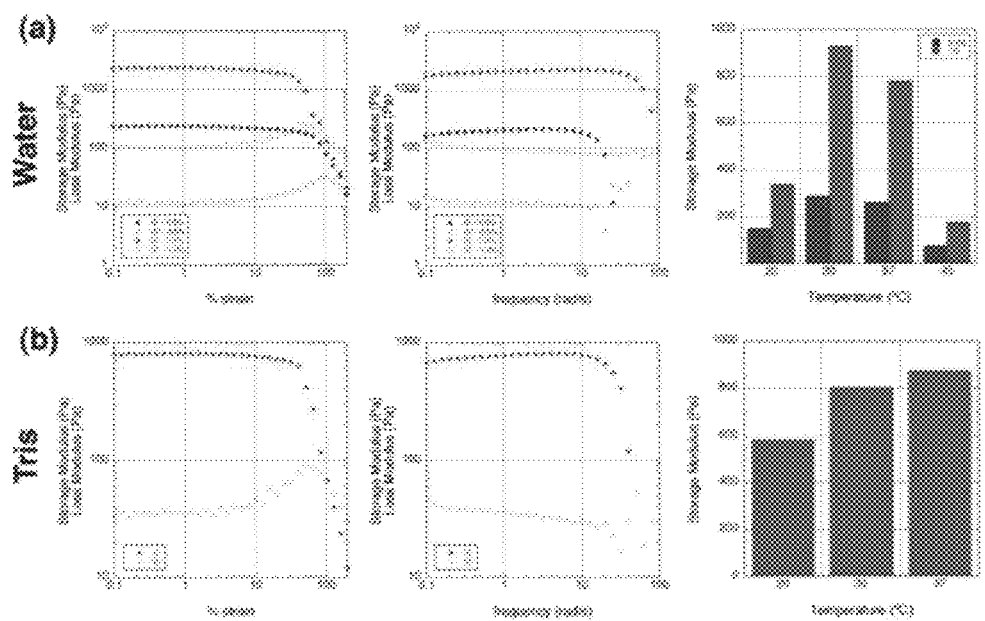

FIG. 18 shows rheology of the collagen-like peptide (Pro-Lys-Gly)$_4$(Pro-Hyp-Gly)$_4$(Asp-Hyp-Gly)$_4$ in (a) water, pH 7 (0.5% and 1.0% by weight concentrations) and (b) Tris, pH 7 (1.0% by weight concentration). The left column shows data from strain sweep studies at 1 rad/s (30° C.), the center column is frequency sweep data at 1% strain (30° C.) and the right column displays the temperature dependence of rheological properties in each buffer (data points acquired at 1 rad/s and 1% strain).

Figure 19:
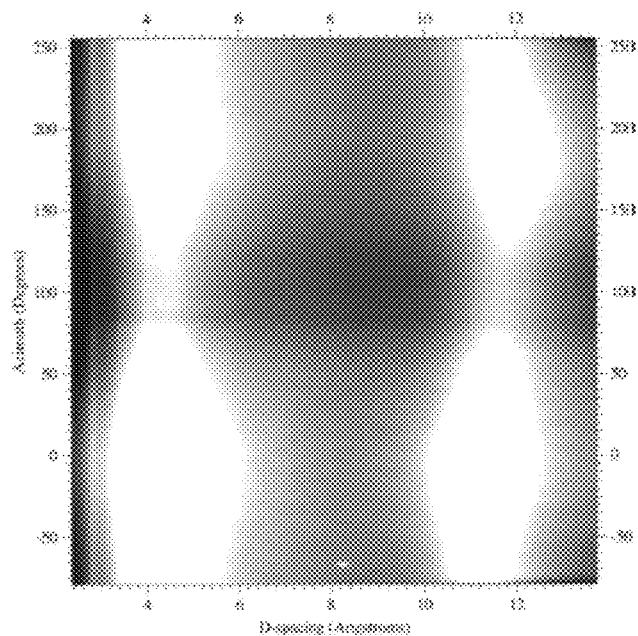

FIG. 19 shows angular dependence of diffraction data. The dried pellet exhibits some alignment as evidenced by the pseudo-2-fold symmetry observed in the intensity versus azimuthal angle scan of the diffraction pattern.

Figure 20:
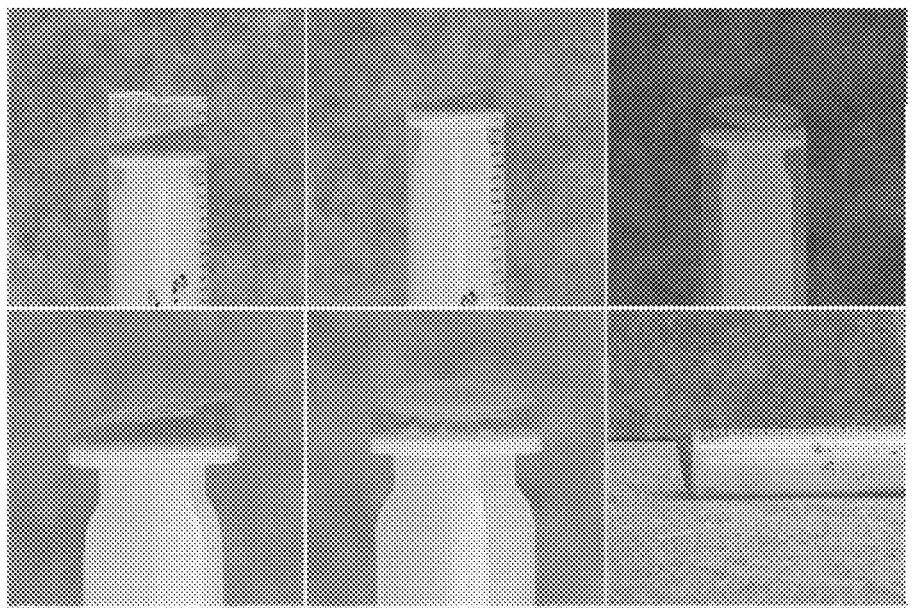

FIG. 20 shows hydrogel of collagen-mimetic peptide as prepared in standard cell culture medium at a concentration of 2.0% by weight. The gel was prepared at a volume of 0.3 ml. The robust nature of the hydrogel and its shape persistence is readily apparent.

The patent or application file contains at least one drawing executed in color. Copies of this patent or patent application publication with color drawing(s) will be provided by the Office upon request and payment of the necessary fee.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure generally relates to collagen, and more particularly compositions and methods related to collagen-mimetic peptides.

The major drawback of systems that utilize harvested collagen is threefold: cost, immune response and lack of system control. Although there are examples of relatively inexpensive forms of collagen available for purchase, for example collagen type I harvested from rat-tail tendon, clinical applications primarily use collagen from bovine, porcine and human sources due to the similarity to human tissue, however these sources are more expensive to obtain. An immune response induced by harvested collagen implants is more intense for xenogeneic tissues (bovine or porcine implants put into humans), however even allogeneic implants (human implants used on another human) show negative immune responses. The majority of reported responses is local to the implantation site and appears as rashes, inflammation and infection. However, there have been reported cases of patient death after the implantation of a harvested collagen-containing system. The root of this immune response stems from the final drawback of harvested collagen systems: the lack of control within the systems. Despite the fact that all harvested tissues are thoroughly cleaned based on their application, all impurities cannot be removed from a sample, their concentration is simply reduced. It is these impurities that include species and individual markers from the donor that result in immune responses in the patient.

In contrast, synthetic collagen systems have high levels of control due to the fact that a bottom-up approach is used for these systems. For clarification, a bottom-up approach uses individual building blocks (molecules, peptides, etc.) that are designed in order to assemble in a certain manner and according to the present disclosure, they assemble to replicate the 3D matrix that native collagen creates within the body. Many peptide-based systems have been designed using a similar approach and have been shown to have extensive potentials for restorative medicine and tissue engineering applications. However, none have discretely replicated the self-assembly of collagen which is the major component of the extracellular matrix that these systems are attempting to mimic. The present disclosure describes a peptide system based on a collagen-mimetic amino acid sequence that assembles following the same steps as collagen to form an organized collagen-mimetic hydrogel network.

Figure 2:
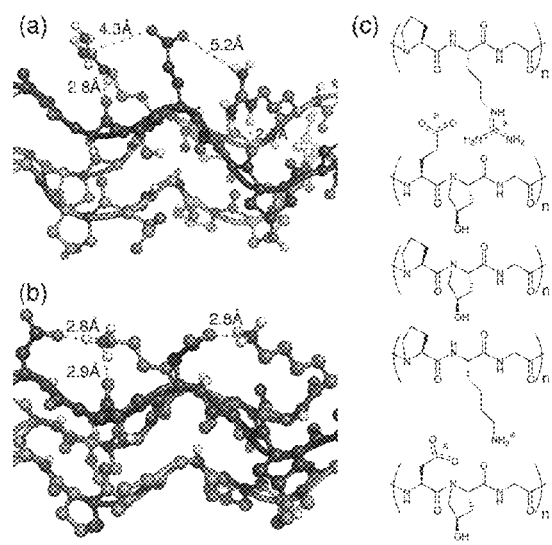

Recently the structure of several of heterotrimeric collagen helices has been investigated by NMR.[18,24] Systems that utilize argininate-glutamate interactions were found to be distant from one another and interact primarily by charge screening rather than by a specific salt-bridged hydrogen bond (FIG. 2a).[24] One of the reasons for this is that the arginine side chain forms a tight hydrogen bond with the backbone carbonyl of an adjacent peptide chain, which restrains it from making more intimate contact with glutamate. In contrast, it was observed that a very high quality formation of lysine-aspartate salt-bridged hydrogen bonds (FIG. 2b).[18] Based on these charge-pair observations, we prepared a new peptide which replaces the arginine residues with lysine and the glutamate residues with aspartate making the sequence (Pro-Lys-Gly)$_4$(Pro-Hyp-Gly)$_4$(Asp-Hyp-Gly)$_4$. More effective interactions between lysine and aspartate previously observed result in superior fiber and hydrogel forming characteristics.

Figure 1:
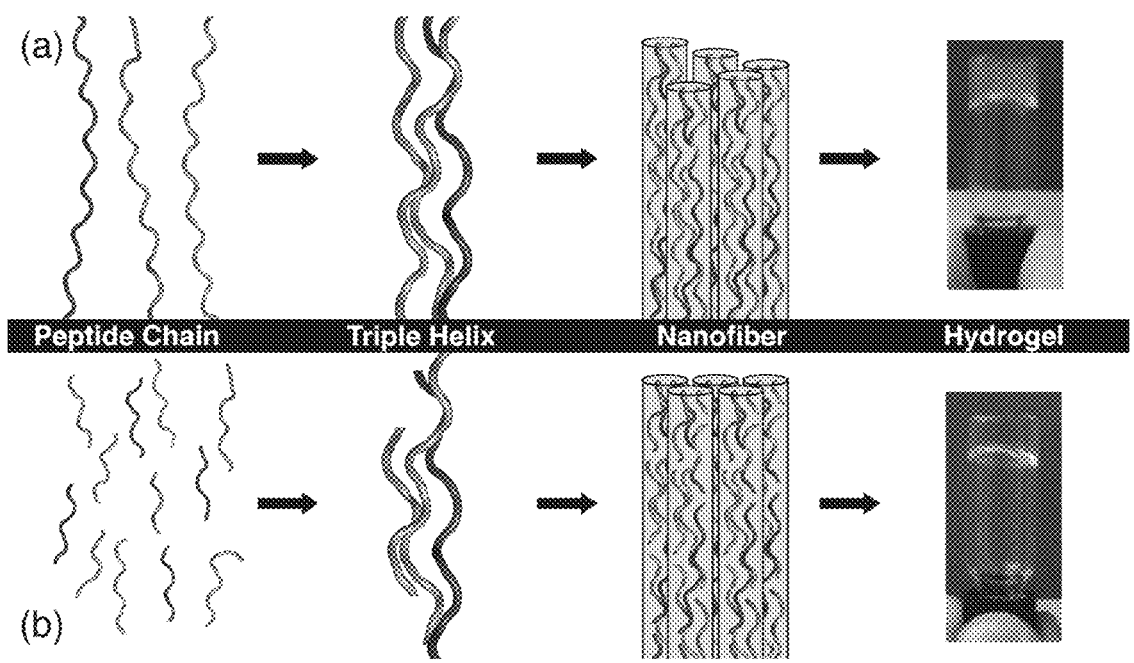

The collagen mimetic peptides of the present disclosure are capable of multi-hierarchical assembly through each level of assembly as depicted in FIG. 1b. The peptides of the present disclosure, in some embodiments, demonstrate substantial control at one or more of each level of collagen assembly: triple helicity, fiber formation, and hydrogel formation. Due, at least in part, to this control, this peptide, as well as systems and methods based upon it, have a large potential for use as scaffolds in restorative medicine and tissue engineering applications. Because this is a designed, synthetic peptide, its amino acid sequence can be easily modified to tailor the peptide more specifically for a particular application, such as, for example, drug delivery, cell delivery, reconstructive surgery, and the like. Additionally, the peptides of the present disclosure reproduce most of the properties of natural collagen while maintaining a high level of system control, which, among other things, may allow for better biocompatibility and the avoidance the major drawbacks of harvested collagen systems. Thus the peptides of the present disclosure may be used as a substitute for natural collagen in multiple restorative medicine applications focused on different tissues throughout the body.

In one embodiment, the present disclosure provides a collagen-mimetic peptide comprising the amino acid sequence (Pro-Lys-Gly)$_4$(Pro-Hyp-Gly)$_4$(Asp-Hyp-Gly)$_4$, (SEQ. ID. NO. 1), where Pro is proline, Lys is lysine, Gly is glycine, Hyp is hydroxyproline and Asp is aspartic acid. This 36 amino acid peptide follows the characteristic X-Y-Gly sequence, which is unique to collagen, allowing for the peptide design to be referred to as collagen-mimetic.

In another embodiment, the present disclosure provides a system comprising a plurality of collagen-mimetic peptides of SEQ. ID. NO. 1. In one embodiment, the present disclosure provides a collagen-mimetic hydrogel comprising peptides of SEQ. ID. NO. 1. The most notable feature of collagen is its multi-hierarchical self-assembly (peptide chain to triple helix to nanofibers and finally a hydrogel). The peptide (Pro-Lys- Gly)$_4$(Pro-Hyp-Gly)$_4$(Asp-Hyp-Gly)$_4$, is characterized by the ability to replicate the self-assembly of collagen through each of the discrete steps. The peptides of the present disclosure successfully demonstrate stable triple helix formation with a melting temperature of 40-41° C. A thermal stability above the body temperature is important for potential use in restorative medicine.

The peptide and systems incorporating the peptide exhibits nanofiber morphologies as observed in atomic force microscopy (AFM), scanning electron microscopy (SEM) and transmission electron microscopy (TEM), including both dry and hydrated techniques, and the nanofibers formed are quite uniform and with virtually no other aggregations or morphologies observed. The inclusion of a hydrated technique, specifically cryo-TEM, demonstrates that the nanofibers seen in dry techniques are not artifacts from drying but are actually present in the solution state. The observed nanofibers are quite uniform with widths of about 4-5 nm, heights of about 1.2±0.3 nm, lengths with a lower bound of hundreds of nanometers and with virtually no other aggregations or morphologies observed.

Furthermore, nanofibrous self-assembly could be easily observed under a wide range of buffers and ionic strengths indicating the robust nature of the self-assembly process. The nanofibers display characteristic triple helical packing confirmed by fiber diffraction and self-assemble into hydrogels with good viscoelastic properties as measured by oscillatory rheology and compared to both natural and synthetic hydrogels. A clear understanding of the viscoelastic properties of a system and how they can be modified is very important for a system's potential use in tissue engineering applications. For this peptide and peptide system, concentration and buffer are the two major variables used to adjust the viscoelastic nature of the hydrogels allowing the modulation of the system for different restorative medicine applications. Finally, the prepared hydrogels were broken down by collagenase type IV at a similar rate to rat-tail collagen in a simple functionality test further demonstrating the potential use of this system for tissue engineering applications.

One advantage of the peptides of the present disclosure as compared to other synthetic scaffolds, is the bio-mimetic assembly of (Pro-Lys-Gly)$_4$(Pro-Hyp-Gly)$_4$(Asp-Hyp-Gly)$_4$. For popular synthetic polymer systems such as polyethylene glycol (PEG) and poly-lactic acid (PLA), many alterations must be made to the structures in order to make the polymers biocompatible and capable of being broken down safely by the body. Therefore the greatest drawback for these systems is that they are not modeled after biologically occurring molecules. For peptide-based systems that use naturally occurring amino acids as the building blocks, PuraMatrix being the most highly used, one concern is their β-sheet forming potential. Many of the systems utilize β-sheets to form the nanofibers, which, within the body, resemble amyloid assemblies that are of concern for restorative medicine applications. In contrast, the peptides of the present disclosure assemble following the same hierarchical process as natural collagen making its safety within the body less controversial than its β-sheet alternatives.

In another embodiment, the present disclosure provides a method comprising preparing a plurality of collagen-mimetic peptides of SEQ. ID. NO. 1; placing the plurality of peptides in a buffer; and allowing the peptides to self-assemble to form a hydrogel. In one embodiment, the peptides of the present disclosure may be prepared by standard solid phase peptide synthesis. After purification by standard HPLC and dialysis, the material undergoes a multi-step self-assembly first forming a triple helices, then fibers and finally a viscoelastic hydrogel. In certain embodiments, the collagen-mimetic peptides may be present in the buffer at a concentrations of from about 0.2% to about 2% by weight. In other embodiments, the collagen-mimetic peptides may be present in the buffer at a concentration of from about 0.5% to about 1% by weight. In other embodiments, the collagen-mimetic peptides may be present in the buffer at concentrations ranging from about 0.6 mM to about 3 mM. One of ordinary skill in the art with the benefit of this disclosure will be able to select a concentration of collagen mimetic peptides to achieve hydrogels of the desired viscoelastic properties.

The buffer used according to the methods of the present disclosure may be any buffer that allows for the self-assembly of the collagen-mimetic peptides of the present disclosure into triple helices, fibers, and hydrogels. In certain embodiments, the buffer may be sodium phosphate, water, Tris, or PBS. In certain embodiments, the buffer is of a pH of about 7. The ionic strength of the buffer may be varied to suit a particular application. In certain embodiments, the density of the fibers formed may be modified depending on the type of buffer used. For example, fibers formed in PBS appeared more dense than fibers in water or Tris. (See FIGS. 15, 16, and 17.) According to the present disclosure, the ability of the peptide to form a hydrogel decreases as ionic strength of the buffer increased. One of ordinary skill in the art with the benefit of this disclosure will be able select an appropriate ionic strength for the buffer to achieve a hydrogel with desired properties.

The peptides of the present disclosure are capable of self-assembling and form a sticky-ended collagen-like triple helix. At sufficient concentration, these triple helices elongate and bundle into a homogeneous population of nanofibers with triple helical packing similar to natural collagen and these nanofibers interact to form high quality hydrogels that are degraded at a similar rate to rat-tail collagen. Thus, the collagen-based system of the present disclosure simultaneously demonstrates triple helix, nanofiber and hydrogel formation and as such, substantially recapitulates the multihierarchical self-assembly of natural collagen. Because of collagen's major role in critical functions such as tissue structure, repair and regeneration, the peptides of the present disclosure, and those based on its design, will play an important role in regenerative medicine and drug delivery.

In another embodiment, the present disclosure provides a biomaterial comprising a collagen-mimetic hydrogel, wherein the hydrogel comprises peptides of SEQ. ID. NO. 1. One example of a hydrogel formed according to the present disclosure is provided in FIG. 20. The peptides of the present disclosure, due to their ability to behave similarly to native collagen, may be used in any application where it would be beneficial to use collagen. For example, in certain embodiments, the peptides and hydrogels of the present disclosure may be used in may different applications, including but not limited to, cosmetic surgery, joint repair, artificial skin grafts, vascular tissue regenerations, scaffolds for tissue engineering applications, and as carriers for drug delivery.

To facilitate a better understanding of the present invention, the following examples of certain aspects of some embodiments are given. In no way should the following examples be read to limit, or define, the entire scope of the invention.

EXAMPLES

Methods

Figure 7:
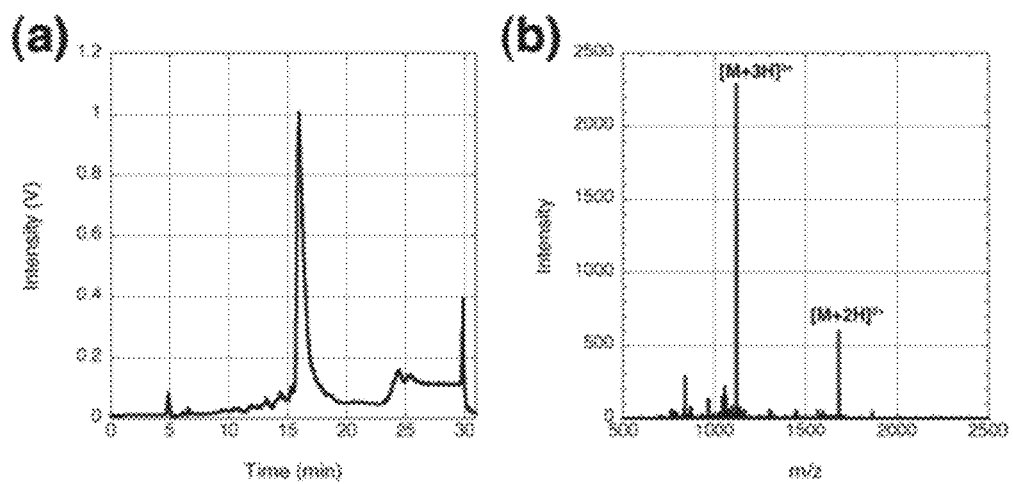

Peptide Synthesis
(Pro-Lys-Gly)$_4$(Pro-Hyp-Gly)$_4$(Asp-Hyp-Gly)$_4$ was synthesized using standard Fmoc chemistry for solid phase peptide synthesis on an Advanced Chemtech Apex 396 multi-peptide automated synthesizer at a scale of 0.15 mM on a glycine pre-loaded Wang resin. Once synthesized, the peptide was purified on a Varian PrepStar220 HPLC using a preparative reverse phase C-18 column then dialyzed against deionized water in order to remove salts. Once dialyzed, the peptide was analyzed by ESI/TOF mass spectrometry on a Bruker microTOF. The HPLC chromatogram and mass spectrum are given in FIG. 7.

Sample Preparation.

All peptide concentrations were measured by weight. All samples were adjusted to pH 7 with sodium hydroxide prior to the addition of buffer and then annealed for 15 minutes at 85° C. Lastly, the samples were incubated at room temperature for at least 12 hours prior to characterization to ensure complete assembly. Time course rheological studies are given in FIG. 13 to support this time scale.

Circular Dichroism.

All spectra and thermal unfolding studies were performed on a Jasco J-810 spectropolarimeter equipped with a Peltier temperature control system. Quartz cells were used with pathlengths of 0.01 cm and 0.1 cm depending on the peptide concentration and buffer. Spectra were collected from 190-250 nm. Melting experiments were performed from 5 to 85° C., monitoring at 225 nm, and the first derivative of the thermal unfolding curve was taken in order to determine the melting temperature of the sample. The molar residual ellipticity (MRE) is calculated from the measured ellipticity using the equation:

$$[\theta] = \frac{\theta \times m}{c \times l \times n_r}$$

where θ is the ellipticity in mdeg, m is the molecular weight in g/mol, c is the concentration in mg/ml, l is the pathlength of the cuvette in cm, and $n_r$ is the number of amino acids in the peptide. The spectrum for 1.0% by weight is only shown from 250-205 nm due to the increase in background noise for higher concentration samples at lower wavelengths.

Atomic Force Microscopy.

Samples were prepared and dropped onto freshly cleaved mica while spinning on a Headway Research, Inc. Photoresist spinner. The sample was quickly rinsed with deionized water for 4-5 seconds and then spun for an additional 10 minutes. AFM images were collected on a Digital Instruments Nanoscope Ma AFM in tapping mode under ambient conditions. Height profiles were obtained using Nanoscope software (20 measurements were taken per peptide concentration and buffer, averaged and the standard deviation calculated).

Transmission Electron Microscopy (TEM).

Samples for TEM were prepared on Quantifoil® R1.2/1.3 holey carbon mesh on copper grids. For dry TEM, phosphotungstic acid (PTA) was used to stain the TEM grids using negative staining techniques. A 2.0% by weight solution of PTA was prepared and adjusted to pH 6 with sodium hydroxide. All stains were made bi-weekly and syringe filtered prior to use. For dry TEM sample preparation, the peptide solution was added to the carbon side of a TEM grid, allowed to dry for one minute, then indirectly blotted with filter paper to remove excess solution. The grid was allowed to dry for 5 minutes before it was inverted onto an aliquot of PTA solution where it remained for 10 minutes. The grid was then placed on filter paper to dry overnight.

Vitreous ice TEM samples were prepared as follows. First, the TEM grids were glow discharged for one minute with a 5 mA discharge on a EMS 100 Glow Discharge Unit. The next stages of sample preparation were performed using a FEI Vitrobot type FP5350/60. The peptide solution (a diluted sample with a concentration of 0.25% by weight made from a 0.5% by weight sample) was added to the grid and immediately blotted for 2 seconds before being immersed in liquid ethane. The grid was then manually transferred from liquid ethane to liquid nitrogen where it was stored until imaging. All TEM imaging was performed on a JEOL 2010 microscope (200 kV) and cryo-imaging was taken at a temperature of −176° C. using low dose conditions.

Scanning Electron Microscopy (SEM).

100 nl aliquots of each gel were placed in a 24-wellplate. Gels were dehydrated in a series of ethanol/water solutions progressing from 30% to 100% ethanol over the course of 24 hours. The dehydrated gels were critical point dried using an Electron Microscopy Sciences 850 critical point drier. They were then affixed to SEM pucks using conductive carbon tape. The pucks were sputter coated with 10 nm gold, rotated, and then sputter coated with an additional 5 nm gold using a CRC-150 sputter coater. Samples were imaged using a FEI Quanta 400 ESEM at 20.00 kV.

Rheology.

All rheological studies were performed on a TA AR-G2 rheometer. Strain and frequency experiments were performed using 12 mm stainless steel parallel plate geometry with a 500 mm gap size. Strain sweeps maintained a fixed frequency (1 rad/s) and a variable strain (0.01-200%). Frequency sweeps utilized a fixed strain (1%) and varying frequencies (0.1-200 rad/s).

X-Ray Fiber Diffraction.

A freshly annealed 1.0 wt % sample was dried by placing 10 nl droplets between two capillaries held in the center of a custom magnet assembly as described by Sunde et. al. over a period of several days.[43] A dried peptide pellet attached to the end of the capillary was used for data collection. Data was collected at 1.54 Å using a Rigaku RUH3R rotating anode x-ray generator with a Rigaku R-axis IV++ detector. The detector was placed at a distance of 180.0 mm from the sample, which was cooled using a $N_2$ stream to 100 K. Diffraction patterns were acquired with exposure times ranging from 1 to 40 minutes, with the highest exposure time yielding the best pattern. The data was analyzed using the Fit2D software package.[54] The position of the beam stop was calculated using the ring 11.5 Å and a median filter was applied to the data. Radial integration was carried out to produce a 1D profile of the observed intensities as a function of D-spacing (A) and angular integration to generate a plot of the observed intensities as a function of D-spacing (A) and azimuthal angle.

Results and Discussion

Once the peptide (Pro-Lys-Gly)$_4$(Pro-Hyp-Gly)$_4$(Asp-Hyp-Gly)$_4$ was successfully synthesized and purified, samples were made at specified concentrations between 0.2% (0.6 mM) and 1.0% (3 mM) by weight. Multiple buffer systems were explored with varying ionic strengths however, we will primarily discuss results in 10 mM sodium phosphate buffer at pH 7 (referred to as phosphate). In this buffer system, all samples made at concentrations of 0.5% (1.5 mM) by weight or higher formed hydrogels within a few hours. Once the observation of hydrogel formation was made, we began systematically analyzing the peptide at each level of self-assembly: triple helix, nanofiber and hydrogel.

Triple Helix.

Figure 3:
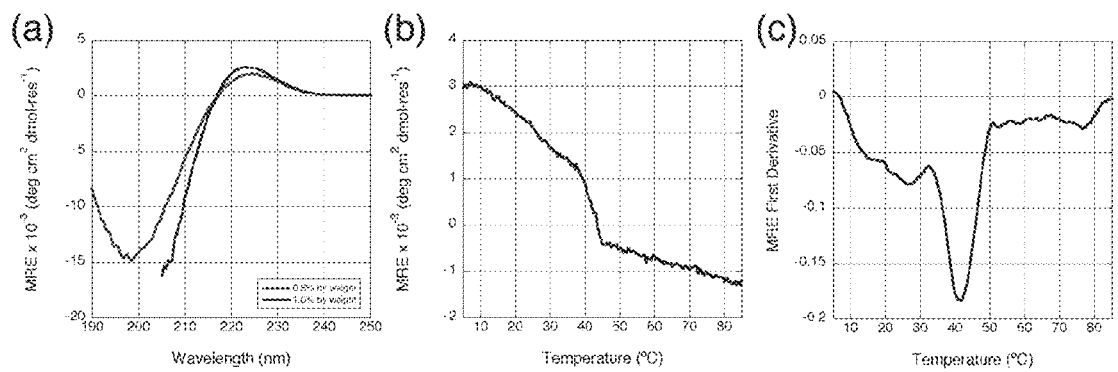
Figure 8:
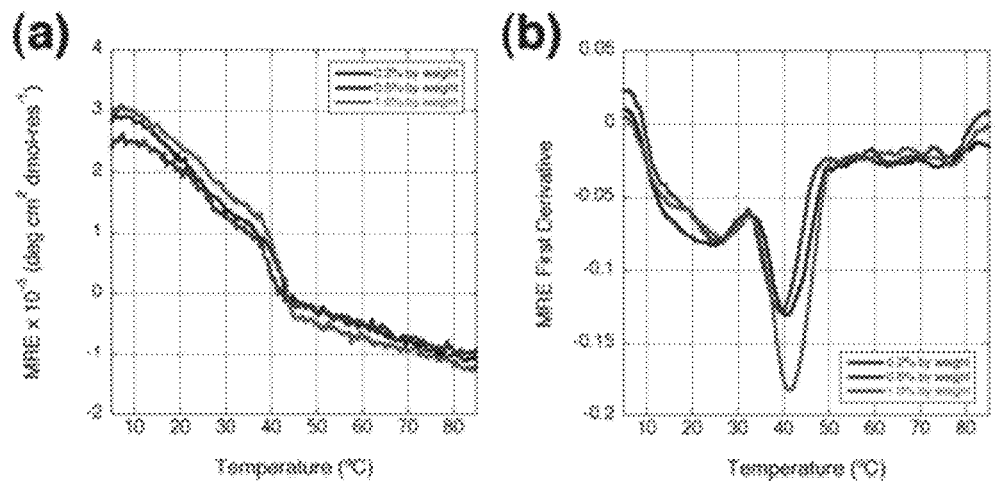
Figure 9:
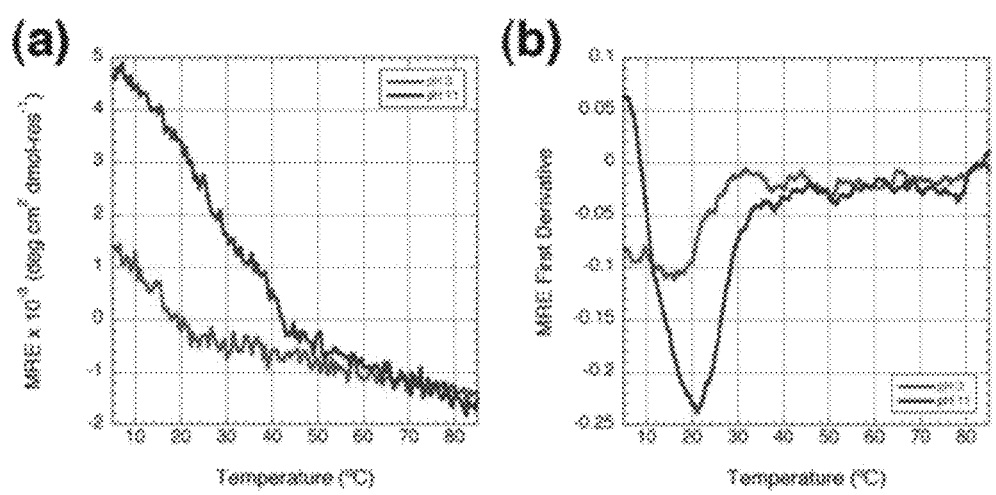
Figure 10:
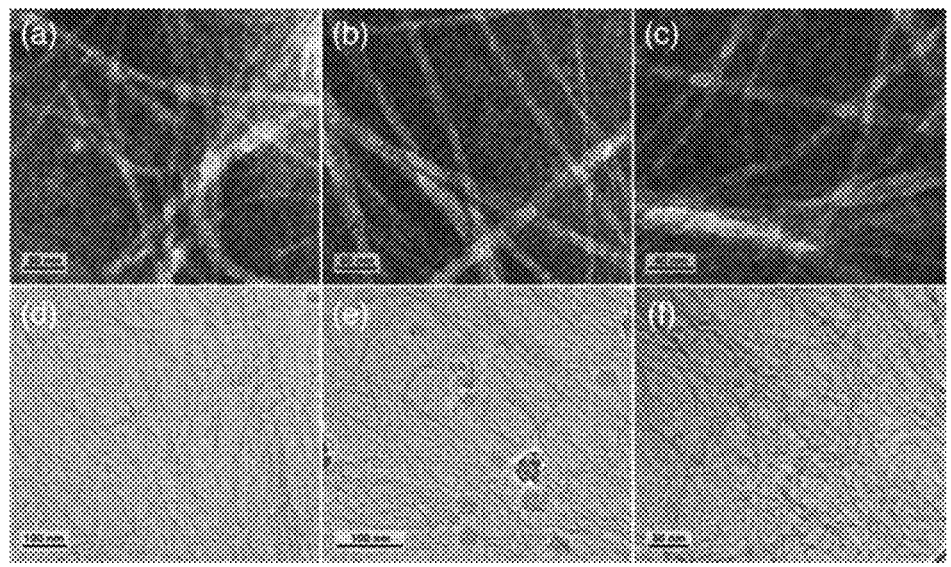

In order to determine whether a collagen mimetic peptide forms a triple helix, two circular dichroism (CD) experiments must be performed: a wavelength spectrum and a thermal unfolding curve. Collagen triple helices have a signature CD spectral profile that consists of a maximum at 225 nm and a minimum near 200 nm which is indicative of a poly-proline type II helix. The thermal unfolding experiment monitors the spectral maximum as temperature is increased which, when a triple helix is present, shows a cooperative transition. For the peptide (Pro-Lys-Gly)$_4$(Pro-Hyp-Gly)$_4$(Asp-Hyp-Gly)$_4$, CD spectra taken at all concentrations showed a strong maximum at 225 nm. The spectra for 0.5% and 1.0% by weight in phosphate are shown in FIG. 3a. Note the size difference in the maximum in the spectrum for 1.0% by weight compared to 0.5% by weight despite the fact that the data is normalized for concentration. This indicates an increased percentage of the peptide is folded at the higher concentration. When melting experiments are performed from 5 to 85° C. on samples at 0.2%, 0.5% and 1.0% by weight concentrations, all samples exhibit a cooperative transition in the melting profile. Additionally, transitions for samples at higher peptide concentrations were stronger and more clear than those for lower concentrations, indicating that the higher concentration of peptide helps to drive triple helix formation. The thermal unfolding curve and the first derivative of the curve for a 1.0% by weight sample in phosphate are shown in FIGS. 3b and 3c respectively. FIG. 10 shows TEM images of the collagen-like nanofibers. (Melting studies for 0.2% and 0.5% by weight are given in FIG. 8 and FIG. 9 shows circular dichroism thermal unfolding curves for (Pro-Lys-Gly)$_4$(Pro-Hyp-Gly)$_4$(Asp-Hyp-Gly)$_4$ in 10 mM phosphate buffer at pH 3 (red) and pH 11 (blue) with a peptide concentration of 1.0% by weight.) A major transition can be seen in the first derivative curve at 40-41° C., corresponding to the melting temperature for the peptide. However, a broad, minor transition is also visible between 10 and 30° C. The minor transition may be due to increased helicity upon fiber elongation and lateral packing. A more detailed explanation for this will be given in the Hydrogel section below.

Nanofiber.

Figure 4:
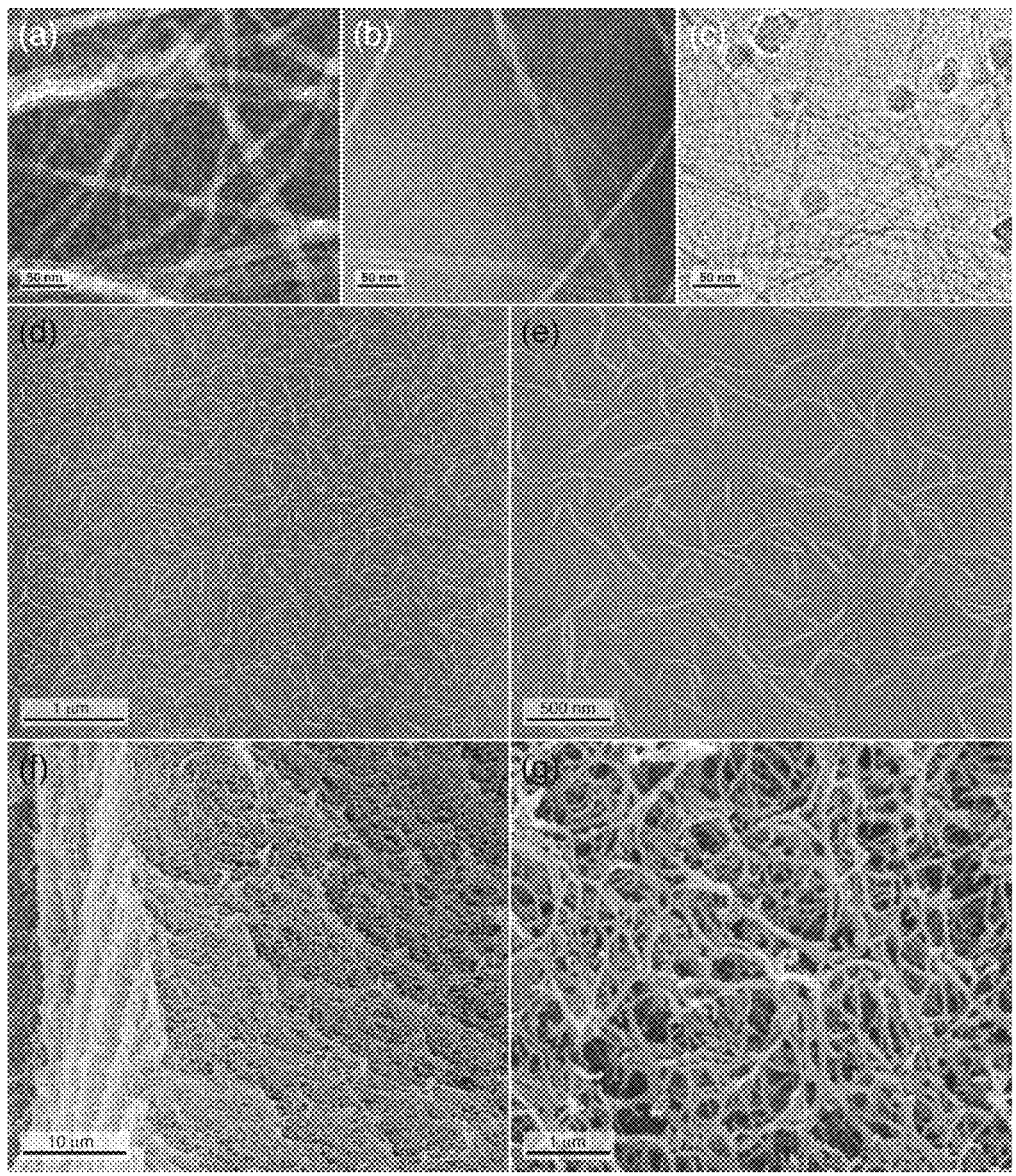
Figure 11:
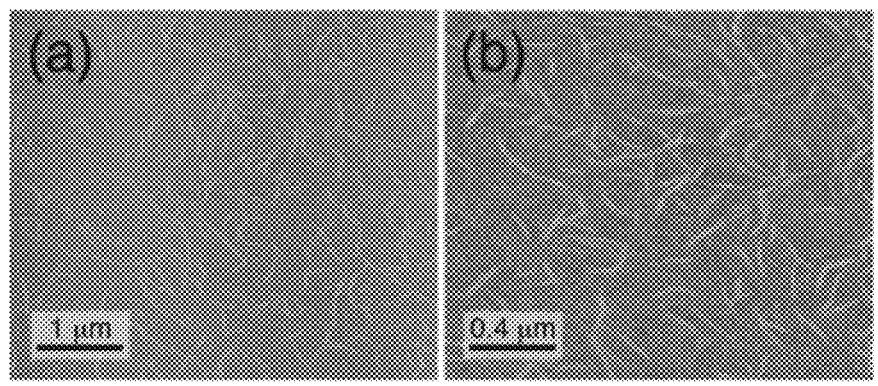
FIG. 11 shows AFM of collagen-like nanofibers in phosphate buffer, pH 7, as observed after spin coating onto freshly cleaved mica at concentrations of (a) 0.5% by weight and (b) 1.0% by weight. This image complements FIGS. 4a and 4b to show further examples of the nanofibers seen by AFM.

Once the triple helical nature of the peptide was confirmed, the next step was to understand the nanostructure of the self-assembled peptide. Multiple microscopy techniques were used including transmission electron microscopy (TEM), atomic force microscopy (AFM) and scanning electron microscopy (SEM). TEM is an integral technique for viewing the morphology and measuring the length and width of structures on the nanoscale. It is most commonly a dry technique that, for viewing carbon-based materials, requires the sample to be stained with a heavy metal such as phosphotungstic acid (PTA). For this peptide, a 1.0% by weight concentration sample in phosphate was prepared using the previously described procedure and negatively stained with PTA. Images of these stained samples (FIGS. 4a and 4b as well as FIG. 11) reveal long nanofibers present both as single fibers and as fiber bundles. FIG. 4a exhibits the variety of fiber widths present within this system when dried and stained. These fibers are the major species within the TEM sample, in contrast to previously reported collagen mimetic nanofibers that show large aggregates and a variety of other non-fibrous structures in the TEM images. FIG. 4b reveals the twisting nature of some of the nanofibers in contrast to fibers with a smoother morphology. Although the negatively stained TEM images show the presence of nanofibers for this peptide system, drying artifacts can cause samples to appear more densely packed or with a completely different structure than what is present in the hydrated state. In addition, the use of a heavy metal stain adds an additional level of uncertainty in assessing fiber size and morphology. For these reasons, we believe the presence of nanofibers in a solution state can only be proven by imaging the system in a hydrated environment, specifically using vitreous ice cryo-TEM.

The sample preparation for cryo-TEM differs greatly from dry TEM due to the fact that cryo-TEM requires a thin aqueous film of sample on the TEM grid before it is flash frozen in ethane slush. A representative TEM image from this preparation is given in FIG. 4c with additional images in FIG. 10. In contrast to the dry TEM images, especially FIG. 4a, the fibers seen in the vitreous ice cryo-TEM sample have uniform widths from 4-5 nm and fiber lengths from several hundred nanometers to many microns. However, similar to the dry TEM images, the observed fibers in cryo-TEM are the majority of the peptide population in the sample. (The spherical species seen in the cryo-TEM image are ethane artifacts that result from sample preparation, not peptide aggregates). Therefore, in both dry and cryo-TEM, the presence of nanofibers was confirmed and they were observed to be the major species within the system. Once the length and width of the nanofibers formed from the peptide was determined from TEM, the height of the fibers was needed in order to understand the mechanism of fiber formation. Tapping mode AFM is the most efficient method for acquiring this data. FIGS. 4d and 4e are AFM images taken of 1.0% and 0.5% by weight samples, respectively, in phosphate buffer. Nanofibers can be seen in both images with the higher concentration sample exhibiting a thicker network of nanofibers. Similar fibers were seen in all buffers examined including higher ionic strength buffers, such as phosphate buffered saline (PBS). The measured height profile in phosphate buffer from the AFM images was 1.2±0.3 nm. This value is much lower than the fiber width of 4-5 nm measured from TEM and the observed fiber lengths seen in AFM also appear smaller than those seen in TEM. A hypothesis for this difference will be discussed below in the Proposed Mechanism of Assembly section. One advantage of these images is that due to their lower magnification, a larger area is observable and the uniformity of the population of self-assembled nanofibers is more apparent.

Figure 12:
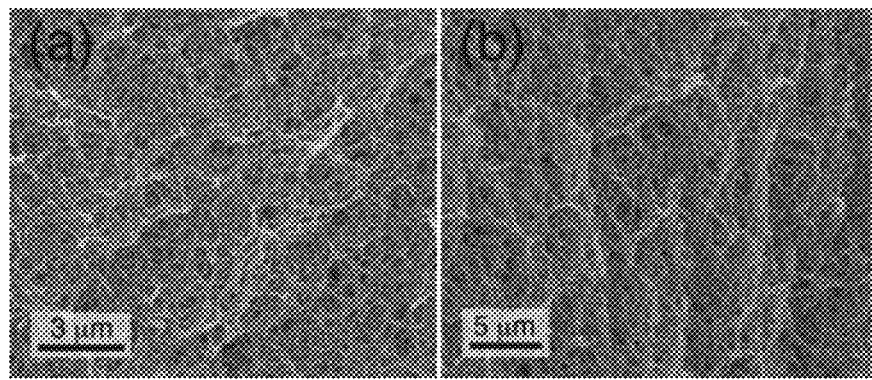
FIG. 12 shows SEM images of critical point dried hydrogel with a peptide concentration of 1.0% by weight showing the interconnected fibrous structure responsible for the gel forming properties at 3,100× (a) and 30,000× (b) magnifications respectively. This figure complements the images in FIGS. 4c and 4d.

One final microscopy method, SEM, is important in understanding the qualitative long-range nanoscale behavior of the system. Samples imaged by SEM were 1.0% by weight in phosphate buffer. In FIG. 4f, the dense fiber network that is homogeneous and extends 10's of microns is apparent. When the magnification is increased (FIG. 4g), the uniform nature of the nanofibers within the network can be more readily seen. FIG. 12 shows additional SEM images. These results directly complement the fiber morphologies observed by TEM and AFM (FIG. 15, FIG. 16, and FIG. 17) and also give an indication of the three-dimensional structure of the hydrogel.

Through the use of multiple microscopy techniques, the nano-morphology of (Pro-Lys-Gly)$_4$(Pro-Hyp-Gly)$_4$(Asp-Hyp-Gly)$_4$ was determined to be nanofibers of relatively uniform dimensions with observed lengths of at least several hundred nanometers, widths of 4-5 nm, measured heights of 1.2±0.3 nm and a uniform long-range behavior visible in the hydrated state.

Hydrogel.

Figure 5:
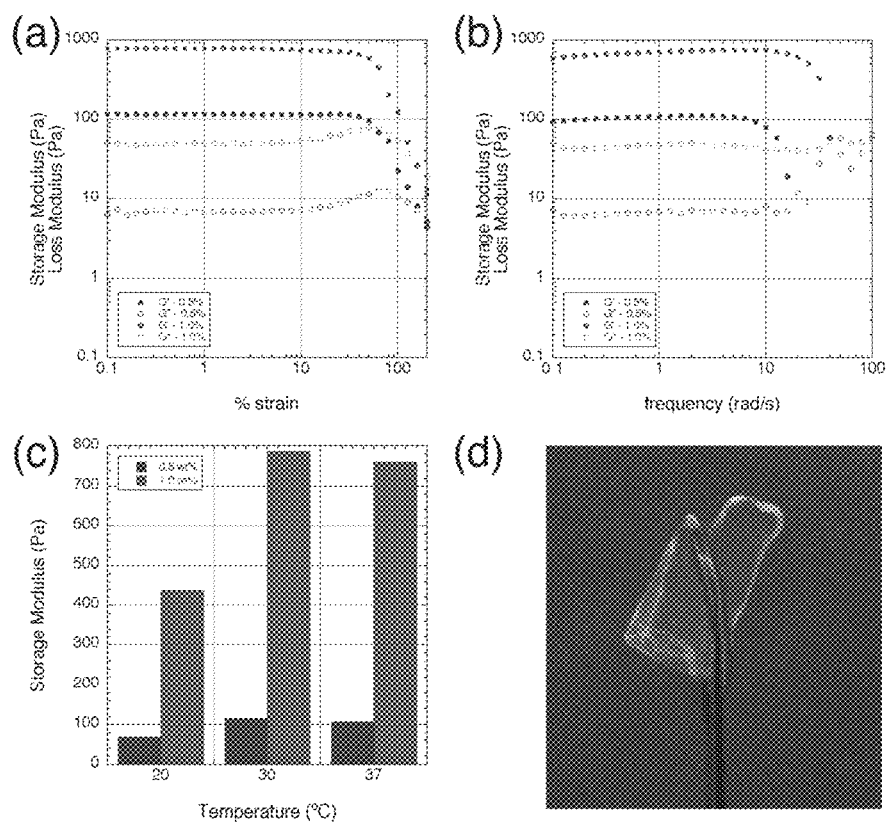

With the first two levels of self-assembly confirmed, the final layer of analysis needed to describe the multi-hierarchical assembly of (Pro-Lys-Gly)$_4$(Pro-Hyp-Gly)$_4$(Asp-Hyp-Gly)$_4$ is the assessment of the visco-elastic properties of the formed hydrogel. Visually, the gels maintain their shape when they have been removed from their containers including the visible sustainability of the gel's sharp edges. The image in FIG. 5d depicts the visual properties of the hydrogel. To quantitatively analyze the peptide hydrogels, rheological studies were performed. Strain and frequency sweep experiments were performed to assess the gel properties and specifically the storage modulus (G') and loss modulus (G") which measure the elastically stored energy and energy lost as heat within the hydrogel respectively. Representative graphs of each type of experiment are shown in FIGS. 5a and 5b respectively, and FIG. 18 shows rheology of collagen-mimetic peptides in water and Tris. The first observation that can be made is that the G' is substantially larger than the G" for both 0.5% and 1.0% by weight concentrations of the peptide in phosphate buffer. Therefore, (Pro-Lys-Gly)$_4$(Pro-Hyp-Gly)$_4$(Asp-Hyp-Gly)$_4$ forms a hydrogel in phosphate buffer at 0.5% by weight concentrations and higher. It should be noted that the observed G' of this collagen mimetic system is similar to that typically observed for a collagen hydrogel formed from natural sources, such as rat tail collagen, despite the fact that our peptide is approximately thirty times shorter (36 amino acids as compared to 1,000).[34] It is also higher than Matrigel[35] and comparable to popular β-sheet hydrogels described in the literature.[36-41]

The collagen mimetic hydrogel was found to be temperature sensitive. From the CD melting studies, we know that the triple helix unfolds at 40-41° C. therefore a temperature ramp rheological experiment from 20 to 60° C. was used to demonstrate the melting of the hydrogel. Indeed, the G' values decreased beginning at 40° C. and by 50° C., the G" values exceed the G' values, which indicates that the gel has disassembled. FIG. 5c is a bar graph representation of the G' values for 0.5% and 1.0% by weight gels in phosphate at 20, 30 and 37° C. The temperatures examined were included in order to gain insight on the behavior of the system before the gel melts. As shown in FIG. 5c, the gels have their highest G' at 30° C. and 37° C. and a substantially lower observed storage modulus at 20° C. The CD melting profile shows a minor transition of the peptide from 10 to 30° C. prior to the actual triple helix unfolding of the system. When we combine the temperature dependent rheological results with the CD data, it suggests that as the peptide slightly unfolds between 10 and 30° C., the unfolded regions of fiber may interdigitate with other nanofibers resulting in the strengthening of the hydrogel.

As a simple functional test of the collagen hydrogel mimetic, we compared its ability to be broken down by collagenase (type IV, Invitrogen) the primary component of which is MMP2, a protease known to specifically cleave between the X and Gly residues of an X-Y-Gly repeat found in a triple helix.[42] (Pro-Lys-Gly)$_4$(Pro-Hyp-Gly)$_4$(Asp-Hyp-Gly)$_4$ hydrogels were prepared at a concentration of 2.0% by weight in phosphate buffer and treated with either collagenase in HBSS (Hank's Balanced Salt Solution) or HBSS alone. The samples were allowed to incubate at room temperature (approximately 20° C.), 30° C. and 37° C. Hydrogels of rat-tail collagen were prepared in the same fashion with and without collagenase. As shown in Tables 1 and 2, hydrogels prepared from our self-assembling peptide and rat-tail collagen degraded at similar rates: samples of both types of hydrogels treated with collagenase were found to be fully dissolved after 1 hour (37° C.) or 4 hours (30° C. and room temperature) while untreated controls were not.

Fiber Diffraction.

Figure 6:
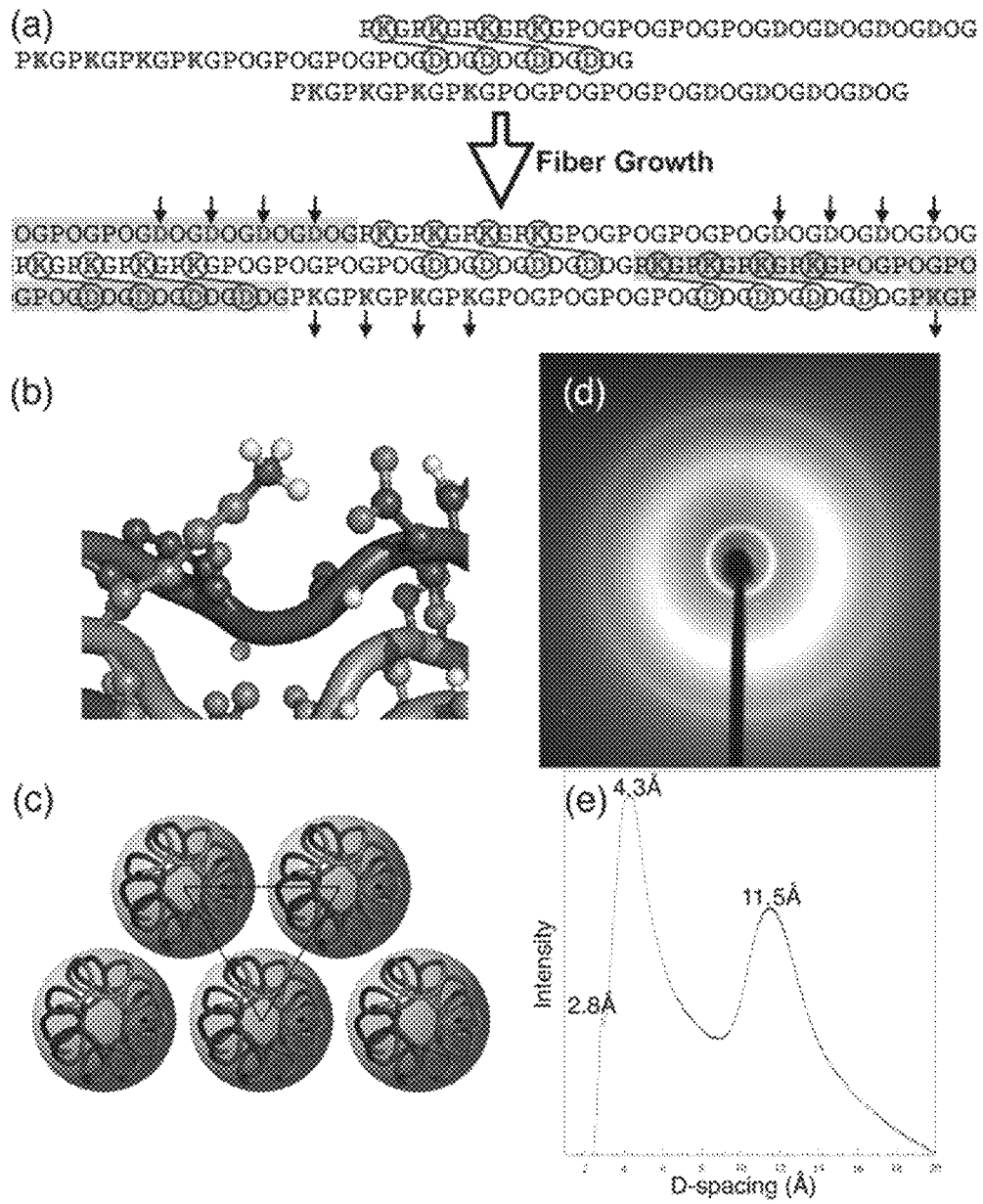

To learn more about the packing morphology of the self-assembled nanofibers, x-ray fiber diffraction studies were carried out on a dried peptide sample (see Methods section for sample preparation). As is apparent from the microscopy images, neighboring fibers lack a common orientation axis. In order to partially align the fibers, the drying peptide solution was placed in a strong magnetic field to promote alignment during the drying process. This methodology has been shown to produce highly aligned protein fibers,[43] but had only limited success in our system. FIG. 6d shows the recorded diffraction pattern. The dried pellet exhibits some alignment as evidenced by the pseudo-2-fold symmetry observed in the intensity versus azimuthal angle scan of the diffraction pattern (see FIG. 19). However, no clear equatorial or meridional axis could be determined and thus the data was analyzed by performing a radial integration of the diffraction pattern to yield a plot of the observed intensities as a function of D-spacing (FIG. 6e). The plot shows three distinct features: a weaker, sharp line near 2.8 Å, a diffuse intense reflection near 4.3 Å and a strong well defined band near 11.5 Å. The spacing of the observed lines agrees well with that observed for collagen from stretched kangaroo-tail tendon.[44] Based this, we assign the 11.5 Å band to the distance between two triple helices inside the nanofibers, the diffuse reflection at 4.3 Å to the distance between peptide chains inside a triple helix and the reflection at 2.8 Å to the translation per triple helical triplet. This suggests that our collagen-like peptide fibers are packing in a fashion similar to natural collagen.

Proposed Mechanism of Assembly.

As mentioned above, the charge pairing of lysine and aspartate has been previously shown to form direct electrostatic interactions in collagen mimetic peptides.[18] Specifically, lysine's side chain reaches in a C-terminal direction to make an intimate salt-bridge hydrogen bond with an aspartate on an adjacent, lagging peptide offset by three amino acids (FIG. 6b). Since our peptide forms a homotrimer, there is a potential for these charged amino acid salt bridges to form between peptide strands and create an offset, sticky-ended triple helix. Similar sticky-ended assemblies have been designed and reported, particularly for alpha-helical coiled coils.[45,46] FIG. 6a shows the proposed repeating unit of peptide self-assembly. Lysine-aspartate interactions are highlighted with purple lassos. This favorable interaction forces a dramatic sticky-ended triple helix in which only one third of the possible lysine-aspartate pairs are satisfied. However, as additional peptides are added to extend the triple helical system, the fraction of satisfied charge pairs increases. For example, adding just one more peptide increases the fraction of satisfied charge pairs to one half and an infinite length triple helical fiber will have two thirds of the salt-bridges satisfied through intra-helical interactions. In addition, for our collagen mimetic system, fiber elongation satisfies a larger percentage of inter-peptide backbone hydrogen bonds donated from glycine which are known to stabilize collagen triple helices.[47-52] In the three peptide nucleation center, only 50% of the glycine residues are capable of forming these inter-peptide interactions however as the fiber grows, the percentage of glycines participating in hydrogen bonds approaches 100%.

As observed by TEM, SEM and AFM, the nanofibers formed have dimensions greater than that of a single collagen triple helix. Therefore, several triple helices must bundle together to form the observed nanofibers. This is backed up by fiber diffraction data which clearly displays the characteristic triple helix packing band at 11.5 Å (FIGS. 6d and 6e). The lysine and aspartate side chains not participating in intrahelix salt-bridges (indicated by small arrows in FIG. 6a) are available for inter-helix interactions which promote helix bundling. In natural collagen, five helices are believed to pack in a quasi-hexagonal fashion to form fibrils that continue to assemble into mature fibers.[1,2] Based on the measured height and width for the (Pro-Lys-Gly)$_4$(Pro-Hyp-Gly)$_4$(Asp-Hyp-Gly)$_4$ nanofibers measured from AFM and cryo-TEM respectively and a helix packing distance from fiber diffraction, we hypothesize that our peptide system assembles in a similar fashion. A schematic of this packing is given in FIG. 6c. The calculated nanofiber height from AFM was found to be 1.2±0.3 nm and the observed nanofiber width from cryo-TEM was 4-5 nm. Both of these measured values are within reason for our proposed quasi-hexagonal packing however, some additional comment on the fiber height should be made. The value measured by AFM appears to be significantly less than expected. There are several possible explanations for this. First, it is known that in AFM, soft organic materials often have measured heights less than expected due to flattening from surface forces or from the AFM tip itself.[53] Another possible explanation is that the triple helices not in direct contact with the mica surface are removed during the washing step leaving behind collagen ribbons only one triple helix high and shorter in length. In fact, our AFM measured height is very nearly exactly what would be expected from a single triple helix. Nevertheless, the bundled fibrous structure is well supported by our x-ray diffraction data and the variances between cryo-TEM, stained TEM, AFM, SEM and x-ray diffraction can be attributed to necessary differences in sample preparation.

Collagenase Degradation Study

Using the previously described gelation procedure, gels of (Pro-Lys-Gly)$_4$(Pro-Hyp-Gly)$_4$(Asp-Hyp-Gly)$_4$ were prepared at a concentration of 2.0% by weight in 10 mM phosphate buffer. Directly after annealing, 100 µl of solution was pipetted into two wells of a 96-well cell culture plate and allowed to incubate at room temperature overnight. A 0.3% by weight collagenase type IV solution was prepared by dissolving 15.0 mg of non-sterile lyophilized enzyme into 5 ml of Hank's Balanced Salt Solution (HBSS). The solution was then filter sterilized using a 0.2 µm filter attached to a syringe. Enzyme and buffer were from Invitrogen (Carlsbad, Calif.). After gelation was complete, 150 µl of collagenase was added on top of one well and 150 µL of HBSS was added on the other serving as a control. Three plates were prepared and incubated at room temperature (about 20° C.), 30° C. and 37° C. Each condition was observed and imaged at 0, 1, 4, 6, 12, 24 and 48 hours after addition of the collagenase or HBSS. Plates containing rat-tail collagen gels at a concentration of 3.0% by weight were prepared and analyzed in an identical manner. Table 1 and Table 2 below show collagenase mediated degradation of (Pro-Lys-Gly)$_4$(Pro-Hyp-Gly)$_4$(Asp-Hyp-Gly)$_4$ and rat-tail collagen hydrogels, respectively. Samples were tested at room temperature (approximately 20° C., 30° C. and 37° C.) with and without collagenase. Both types of hydrogels treated with collagenase were found to be fully dissolved after 1 hour (37° C.) or 4 hours (30° C. and room temperature). Control samples of (Pro-Lys-Gly)$_4$(Pro-Hyp-Gly)$_4$(Asp-Hyp-Gly)$_4$ at room temperature and 30° C. were intact after 48 hours. However at 37° C. the hydrogels dissolved after 24 hours due to the proximity of this temperature to the triple helices melting temperature. Rat-tail collagen controls at 20° C. and 37° C. remained intact at all time points, however at 30° C. the hydrogel was dispersed (though not dissolved) due to handling.

TABLE 1

Degradation of (Pro-Lys-Gly)$_4$(Pro-Hyp-Gly)$_4$(Asp-Hyp-Gly)$_4$

| | (Pro-Lys-Gly)$_4$(Pro-Hyp-Gly)$_4$(Asp-Hyp-Gly)$_4$ | | | (Pro-Lys-Gly)$_4$(Pro-Hyp-Gly)$_4$(Asp-Hyp-Gly)$_4$ w/ collagenase | | |
|---|---|---|---|---|---|---|
| time | 20° C. | 30° C. | 37° C. | 20° C. | 30° C. | 37° C. |
| 0 h | intact | intact | intact | intact | intact | intact |
| 1 h | intact | intact | intact | intact | intact | dissolved |
| 4 h | intact | intact | intact | dissolved | dissolved | dissolved |
| 6 h | intact | intact | intact | dissolved | dissolved | dissolved |
| 12 h | intact | intact | intact | dissolved | dissolved | dissolved |
| 24 h | intact | intact | dissolved | dissolved | dissolved | dissolved |
| 48 h | intact | intact | dissolved | dissolved | dissolved | dissolved |

TABLE 2

Degradation of Rat-Tail Collagen

| | Rat-tail Collagen | | | Rat-tail Collagen w/ collagenase | | |
|---|---|---|---|---|---|---|
| time | 20° C. | 30° C. | 37° C. | 20° C. | 30° C. | 37° C. |
| 0 h | intact | intact | intact | intact | intact | intact |
| 1 h | intact | intact | intact | intact | intact | dissolved |
| 4 h | intact | intact | intact | dissolved | dissolved | dissolved |
| 6 h | intact | dispersed | intact | dissolved | dissolved | dissolved |
| 12 h | intact | dispersed | intact | dissolved | dissolved | dissolved |
| 24 h | intact | dispersed | intact | dissolved | dissolved | dissolved |
| 48 h | intact | dispersed | intact | dissolved | dissolved | dissolved |

Peptide Assembly in Additional Buffers

We explored the self-assembly of (Pro-Lys-Gly)$_4$(Pro-Hyp-Gly)$_4$(Asp-Hyp-Gly)$_4$ in multiple buffers. The buffer library attempted to include a range of ionic strengths and all buffers were made at pH 7. The buffers examined are water (these samples were pH adjusted prior to final dilution in order to ensure accurate pH), Tris (10 mM tris(hydroxymethyl)-aminomethane, pH 7) and PBS (10 mM phosphate, 150 mM sodium chloride, pH 7). Samples at 0.5% and 1.0% by weight concentrations of peptide were prepared in each of these buffers and examined for triple helical stability using CD and nanofiber formation via AFM. In addition, for the samples that formed hydrogels, rheological studies were performed to assess the gel properties. The results from these experiments are given in the figures below. The ability of the peptide to form a hydrogel decreased as ionic strength increased. For example, both peptide concentrations formed hydrogels in water and only 1.0% by weight samples formed a hydrogel in Tris after the standard 12 hour incubation. PBS samples gel very slowly, requiring more than a week for a 1.0% by weight sample. This result directly complemented what was seen in the CD studies because gel-forming samples showed a melting transition at 40-41° C. while samples that did not form gels had a melting temperature around 23° C. These melting experiments are shown in FIG. 14. Despite gelation or triple helical results, all samples made in these buffers formed nanofibers visible by AFM. The fibers in PBS appear more dense than the water or Tris samples however they seem to be shorter in length than the fibers composing the gelled samples. The measured height profiles for each buffer were similar to the heights seen in the phosphate samples and are listed in the figure captions for the AFM images in each buffer.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

REFERENCES

1. Ottani, V., Martini, D., Franchi, M., Ruggeri, A. & Raspanti, M. Hierarchical structures in fibrillar collagens. *Micron* 33, 587-596 (2002).
2. Ottani, V., Raspanti, M. & Ruggeri, A. Collagen structure and functional implications. *Micron* 32, 251-260 (2001).
3. Pinkas, D. M., Ding, S., Raines, R. T. & Barron, A. E. Tunable, post-translational hydroxylation of collagen domains in *Escherichia coli*. *ACS Chemical Biology* 6, 320-324 (2011).
4. Buechter, D. D. et al. Co-translational incorporation of Trans-4-hydroxyproline into recombinant proteins in bacteria. *J. Biol. Chem.* 278, 645-650 (2003).
5. Kohrer, C., Xie, L., Kellerer, S., Varshney, U. & Rajbhandary, U. L. Import of amber and ochre suppressor tRNAs into mammalian cells: A general approach to site-specific insertion of amino acid analogues into proteins. *Proc. Natl. Acad. Sci. USA* 98, 14310-14315 (2001).
6. Liu, D. R., Magliery, T. J., Pasternak, M. & Schultz, P. G. Engineering a tRNA and aminoacyl-tRNA synthetase for the site-specific incorporation of unnatural amino acids into proteins in vivo. *Proc. Natl. Acad. Sci. USA* 94, 10092-10097 (1997).
7. Liu, D. R. & Schultz, P. G. Progress toward the evolution of an organism with an expanded genetic code. *Proc. Natl. Acad. Sci. USA* 96, 4780-4785 (1999).
8. Mendel, D., Cornish, V. W. & Schultz, P. G. Site-directed mutagenesis with an expanded genetic-code. *Annu. Rev. Bioph. Biom.* 24, 435-462 (1995).
9. Boudko, S. P. et al. Crystal structure of human type III collagen Gly991-Gly1032 cystine knot-containing peptide shows both 7/2 and 10/3 triple helical symmetries. *J. Biol. Chem.* 283, 32580-32589 (2008).
10. Kar, K. et al. Aromatic interactions promote self-association of collagen triple-helical peptides to higher-order structures. *Biochemistry* 48, 7959-7968 (2009).
11. Kramer, R. Z., Bella, J., Brodsky, B. & Berman, H. M. The crystal and molecular structure of a collagen-like peptide with a biologically relevant sequence. *J. Mol. Biol.* 311, 131-147 (2001).
12. Krishna, O. D. & Kiick, K. L. Supramolecular assembly of electrostatically stabilized, hydroxyproline-lacking collagen-mimetic peptides. *Biomacromolecules* 10, 2626-2631 (2009).
13. Persikov, A. V., Ramshaw, J. A., Kirkpatrick, A. & Brodsky, B. Amino acid propensities for the collagen triple-helix. *Biochemistry* 39, 14960-14967 (2000).
14. Persikov, A. V., Ramshaw, J. A. M., Kirkpatrick, A. & Brodsky, B. Electrostatic interactions involving lysine make major contributions to collagen triple-helix stability. *Biochemistry* 44, 1414-1422 (2005).
15. Sakakibara, S. et al. Synthesis of (Pro-Hyp-Gly)$_n$ of defined molecular-weights—evidence for stabilization of collagen triple helix by hydroxyproline. *Biochim. Biophys. Acta* 303, 198-202 (1973).
16. Shah, N. K., Ramshaw, J. A., Kirkpatrick, A., Shah, C. & Brodsky, B. A host-guest set of triple-helical peptides: stability of Gly-X-Y triplets containing common nonpolar residues. *Biochemistry* 35, 10262-10268 (1996).
17. Venugopal, M. G., Ramshaw, J. A., Braswell, E., Zhu, D. & Brodsky, B. Electrostatic interactions in collagen-like triple-helical peptides. *Biochemistry* 33, 7948-7956 (1994).
18. Fallas, J. A., Gauba, V. & Hartgerink, J. D. Solution structure of an ABC collagen heterotrimer reveals a single-register helix stabilized by electrostatic interactions. *J. Biol. Chem.* 284, 26851-26859 (2009).
19. Gauba, V. & Hartgerink, J. D. Self-assembled heterotrimeric collagen triple helices directed through electrostatic interactions. *J. Am. Chem. Soc.* 129, 2683-2690 (2007).
20. Gauba, V. & Hartgerink, J. D. Surprisingly high stability of collagen ABC heterotrimer: evaluation of side chain charge pairs. *J. Am. Chem. Soc.* 129, 15034-15041 (2007).
21. Gauba, V. & Hartgerink, J. D. Synthetic collagen heterotrimers: structural mimics of wild type and mutant collagen type I. *J. Am. Chem. Soc.* 130, 7509-7515 (2008).
22. Madhan, B., Xiao, J. X., Thiagarajan, G., Baum, J. & Brodsky, B. NMR monitoring of chain-specific stability in heterotrimeric collagen peptides. *J. Am. Chem. Soc.* 130, 13520-13521 (2008).
23. Ottl, J. et al. Design and synthesis of heterotrimeric collagen peptides with a built-in cystine-knot. Models for collagen catabolism by matrix-metalloproteases. *FEBS Lett.* 398, 31-36 (1996).
24. Russell, L. E., Fallas, J. A. & Hartgerink, J. D. Selective assembly of a high stability AAB collagen heterotrimer. *J. Am. Chem. Soc.* 132, 3242-3243 (2010).
25. Cejas, M. A. et al. Thrombogenic collagen-mimetic peptides: Self-assembly of triple helix-based fibrils driven by hydrophobic interactions. *Proc. Natl. Acad. Sci. USA* 105, 8513-8518 (2008).
26. Kar, K. et al. Self-association of collagen triple helix peptides into higher order structures. *J. Biol. Chem.* 281, 33283-33290 (2006).
27. Kar, K., Wang, Y. H. & Brodsky, B. Sequence dependence of kinetics and morphology of collagen model peptide self-assembly into higher order structures. *Protein Sci.* 17, 1086-1095 (2008).

28. Kotch, F. W. & Raines, R. T. Self-assembly of synthetic collagen triple helices. *Proc. Natl. Acad. Sci. USA* 103, 3028-3033 (2006).
29. Paramonov, S. E., Gauba, V. & Hartgerink, J. D. Synthesis of collagen-like peptide polymers by native chemical ligation. *Macromolecules* 38, 7555-7561 (2005).
30. Yamazaki, C. M., Asada, S., Kitagawa, K. & Koide, T. Artificial collagen gels via self-assembly of de novo designed peptides. *Biopolymers* 90, 816-823 (2008).
31. Skrzeszewska, P. J. et al. Physical gels of telechelic triblock copolymers with precisely defined junction multiplicity. *Soft Matter* 5, 2057-2062 (2009).
32. Rele, S. et al. D-periodic collagen-mimetic microfibers. *J. Am. Chem. Soc.* 129, 14780-14787 (2007).
33. Banwell, E. F. et al. Rational design and application of responsive alpha-helical peptide hydrogels. *Nat. Mater.* 8, 596-600 (2009).
34. Yang, Y. L., Leone, L. M. & Kaufman, L. J. Elastic Moduli of Collagen Gels Can Be Predicted from Two-Dimensional Confocal Microscopy. *Biophys. J.* 97, 2051-2060 (2009).
35. Mi, K. et al. Influence of a self-assembling peptide, RADA16, compared with collagen I and Matrigel on the malignant phenotype of human breast cancer cells in 3D cultures and in vivo. *Macromol. Biosci.* 9, 437-443 (2009).
36. Greenfield, M. A., Hoffman, J. R., de, l. C., MO & Stupp, S. I. Tunable mechanics of peptide nanofiber gels. *Langmuir* 26, 3641-3647 (2010).
37. Yokoi, H., Kinoshita, T. & Zhang, S. Dynamic reassembly of peptide RADA16 nanofiber scaffold. *Proc. Natl. Acad. Sci. USA* 102, 8414-8419 (2005).
38. Zhang, S. G. et al. Self-complementary oligopeptide matrices support mammalian-cell attachment. *Biomaterials* 16, 1385-1393 (1995).
39. Lamm, M. S., Rajagopal, K., Schneider, J. P. & Pochan, D. J. Laminated morphology of nontwisting beta-sheet fibrils constructed via peptide self-assembly. *J. Am. Chem. Soc.* 127, 16692-16700 (2005).
40. Ozbas, B., Kretsinger, J., Rajagopal, K., Schneider, J. P. & Pochan, D. J. Salt-triggered peptide folding and consequent self-assembly into hydrogels with tunable modulus. *Macromolecules* 37, 7331-7337 (2004).
41. Aulisa, L., Dong, H. & Hartgerink, J. D. Self-assembly of multidomain peptides: sequence variation allows control over cross-linking and viscoelasticity. *Biomacromolecules* 10, 2694-2698 (2009).
42. Ottl, J. et al. Recognition and catabolism of synthetic heterotrimeric collagen peptides by matrix metalloproteinases. *Chem. Biol.* 7, 119-132 (2000).
43. Serpell, L. C., Fraser, P. E. & Sunde, M. X-ray fiber diffraction of amyloid fibrils. *Method. Enzymol.* 309, 526-536 (1999).
44. Okuyama, K. Revisiting the molecular structure of collagen. *Connect. Tissue. Res.* 49, 299-310 (2008).
45. Pandya, M. J. et al. Sticky-end assembly of a designed peptide fiber provides insight into protein fibrillogenesis. *Biochemistry* 39, 8728-8734 (2000).
46. Woolfson, D. N. Building fibrous biomaterials from alpha-helical and collagen-like coiled-coil peptides. *Biopolymers* 94, 118-127 (2010).
47. Bella, J., Eaton, M., Brodsky, B. & Berman, H. M. Crystal and molecular structure of a collagen-like peptide at 1.9 Å resolution. *Science* 266, 75-81 (1994).
48. Okuyama, K., Okuyama, K., Arnott, S., Takayanagi, M. & Kakudo, M. Crystal and molecular structure of a collagen-like polypeptide (Pro-Pro-Gly)10. *J. Mol. Biol.* 152, 427-443 (1981).
49. Pauling, L. & Corey, R. B. The structure of fibrous protein of the collagen-gelatin group. *Proc. Natl. Acad. Sci. USA* 37, 272-281 (1951).
50. Ramachandra, G. N. & Kartha, G. Structure of collagen. *Nature* 176, 593-595 (1955).
51. Ramachandran, G. N. & Kartha, G. Structure of collagen. *Nature* 174, 269-270 (1954).
52. Rich, A. & Crick, F. H. C. Molecular structure of collagen. *J. Mol. Biol.* 3, 483-506 (1961).
53. Ruozi, B., Tosi, G., Leo, E. & Vandelli, M. A. Application of atomic force microscopy to characterize liposomes as drug and gene carriers. *Talanta* 73, 12-22 (2007).
54. Wess, T. J., Hammersley, A., Wess, L. & Miller, A. Type-I collagen packing, conformation of the triclinic unit-cell. *J. Mol. Biol.* 248, 487-493 (1995).

What is claimed is:

1. A collagen-mimetic peptide of SEQ. ID. NO. 1.

2. A collagen-mimetic hydrogel comprising a peptide, the peptide comprising the sequence of SEQ. ID. NO. 1.

3. The hydrogel of claim 2, wherein the hydrogel is biocompatible.

4. The hydrogel of claim 2, wherein the hydrogel is viscoelastic.

5. A method of preparing a collagen-mimetic hydrogel comprising:
    obtaining a plurality of collagen-mimetic peptides, wherein each of the plurality of collagen-mimetic peptides comprise the peptide sequence of SEQ ID NO: 1;
    placing the plurality of collagen-mimetic peptides in a buffer; and
    allowing the plurality of collagen-mimetic peptides to self-assemble to form the collagen-mimetic hydrogel.

6. The method of claim 5, wherein allowing the peptides to self-assemble to form a hydrogel comprises allowing the peptides to self-assemble to form a plurality of triple helices.

7. The method of claim 6, wherein allowing the peptides to self-assemble to form a hydrogel comprises allowing the triple helices to self-assemble to form a plurality of fibers.

8. The method of claim 7, wherein allowing the peptides to self-assemble to form a hydrogel comprises allowing the plurality of fibers to self-assemble to form a hydrogel network.

9. The method of claim 5, wherein preparing a plurality of collagen-mimetic peptides comprises solid phase peptide synthesis.

10. The method of claim 5 wherein the buffer is sodium phosphate, water, Tris, or PBS.

11. The method of claim 5, wherein the plurality of collagen-mimetic peptides are placed in the buffer at a concentration of from about 0.5% to about 2% by weight.

12. The method of claim 5, wherein the buffer is of a pH of about 7.

13. A biomaterial comprising a collagen-mimetic hydrogel, wherein the hydrogel comprises a peptide comprising the sequence of SEQ. ID. NO. 1.

14. The biomaterial of claim 13, wherein the biomaterial is a scaffold for tissue engineering applications.

15. The biomaterial of claim 13, wherein the biomaterial is biocompatible.

* * * * *

UNITED STATES PATENT AND TRADEMARK OFFICE
CERTIFICATE OF CORRECTION

PATENT NO. : 9,228,009 B2
APPLICATION NO. : 14/176235
DATED : January 5, 2016
INVENTOR(S) : Jeffrey D. Hartgerink and Lesley R. O'Leary It is certified that error appears in the above-identified patent and that said Letters Patent is hereby corrected as shown below:

In the Specification

On Column 2, Line 22, please add the following sentences:
The development of this invention was funded in part by the Welch Foundation Grant No. C-1557. This material is based in part upon work supported by the Texas Norman Hackerman Advanced Research Program under Grant No. 02000.

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 1

<210> SEQ ID NO 1
<211> LENGTH: 36
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: 14, 17, 20, 23, 26, 29, 32, 35
<223> OTHER INFORMATION: 4Hyp

<400> SEQUENCE: 1

Pro Lys Gly Pro Lys Gly Pro Lys Gly Pro Lys Gly Pro Pro Gly Pro
 1               5                  10                  15

Pro Gly Pro Pro Gly Pro Pro Gly Asp Pro Gly Asp Pro Gly Asp Pro
                20                  25                  30

Gly Asp Pro Gly
            35
```